(12) United States Patent
Maine et al.

(10) Patent No.: US 7,901,910 B2
(45) Date of Patent: Mar. 8, 2011

(54) EMBEDDED EXPRESSION OF INSOLUBLE HETEROLOGOUS PROTEINS

(76) Inventors: Gregory Thomas Maine, Gurnee, IL (US); Linda Ellen Chovan, Wisconsin, WI (US)

( * ) Notice: Subject to any disclaimer, the term of this patent is extended or adjusted under 35 U.S.C. 154(b) by 1383 days.

(21) Appl. No.: 08/742,619

(22) Filed: Nov. 1, 1996

(65) Prior Publication Data

US 2005/0277178 A1 Dec. 15, 2005

(51) Int. Cl.
*C12N 15/09* (2006.01)

(52) U.S. Cl. ............. 435/69.7; 435/69.1; 435/69.3; 536/23.1; 536/23.4

(58) Field of Classification Search ............. 435/69.3, 435/69.1, 69.7, 172.3, 320.1; 536/23.1
See application file for complete search history.

(56) References Cited

FOREIGN PATENT DOCUMENTS

| | | |
|---|---|---|
| EP | 0 331 961 | 9/1989 |
| EP | 0 335 737 | 2/1990 |
| WO | WO 92/13955 | * 8/1992 |
| WO | WO92/13955 | 8/1992 |
| WO | WO95/16044 | 6/1995 |
| WO | WO96/01321 | 1/1996 |

OTHER PUBLICATIONS

L. Hedegaard et al., "Type 1 fimbriae of *Escherichia coli* as carriers of heterologous antigenic sequences", Gene, Dec. 21, 1989, No. 1, Amsterdam, NL.

* cited by examiner

*Primary Examiner* — Robert A Zeman
(74) *Attorney, Agent, or Firm* — Cheryl L. Becker; Dianne Casuto

(57) ABSTRACT

A method for expressing a heterologous protein in a prokaryotic host cell, comprising the steps of:
(a) providing a DNA vector having:
(1) a control region operatively linked to a first genetic element encoding a carrier protein capable of expression in the host cell, and
(2) a second genetic element encoding the heterologous protein, the second element being embedded within the first element such that the first and second elements are contiguous and in the same reading frame;
(b) transforming the host cell with the DNA vector; and
(c) expressing a fusion protein of the heterologous protein and the carrier protein, wherein the heterologous protein is joined at its N-terminus to a first domain of the carrier protein and at its C-terminus to a second domain of the carrier protein, and also a method for confirming intact expression of heterologous proteins, as well as fusion proteins, DNA constructs, plasmid vectors and transformed host cells relating to the above methods.

22 Claims, 17 Drawing Sheets

```
            SalI
      MluI  ▼   MluI
       ▼    ▼    ▼
CCCGCGCTACGCGTCGACGCGTCTGCCC
ProAlaArgTyrAlaSerThrArgLeuPro
```

FIG.9B

```
5' CGCGACGT 3'
3'     TGCAGCGC 5'
```

FIG.9C

```
CCCGCGCGCTACGCGACGTCGCGTCTGCCC
ProAlaArgTyrAlaThrSerArgLeuPro
```

FIG.9D

```
              10         20         30         40
          1234567890 1234567890 1234567890 1234567890
          GAATTAATTC CCATTAATGT GAGTTAGCTC ACTCATTAGG      40

CACCCCAGGC TTTACACTTT ATGTTCCGGC TCGTATTTTG      80

TGTGGAATTG TGAGCGGATA ACAATTGGGC ATCCAGTAAG     120

GAGGTTTAAA TGAGTTTTGT GGTCATTATT CCCGCGCGCT     160
                   M etSerPheVa lValIleIle ProAlaArgT

ACGCGTCGAC GCGTCTGCCC GGTAAACCAT TGGTTGATAT     200
          yrAlaSerTh rArgLeuPro GlyLysProL euValAspIl

TAACGGCAAA CCCATGATTG TTCATGTTCT TGAACGCGCG     240
          eAsnGlyLys ProMetIleV alHisValLe uGluArgAla

CGTGAATCAG GTGCCGAGCG CATCATCGTG GCAACCGATC     280
          ArgGluSerG lyAlaGluAr gIleIleVal AlaThrAspH

ATGAGGATGT TGCCCGCGCC GTTGAAGCCG CTGGCGGTGA     320
          isGluAspVa lAlaArgAla ValGluAlaA laGlyGlyGl

AGTATGTATG ACGCGCGCCG ATCATCAGTC AGGAACAGAA     360
          uValCysMet ThrArgAlaA spHisGlnSe rGlyThrGlu

CGTCTGGCGG AAGTTGTCGA AAAATGCGCA TTCAGCGACG     400
          ArgLeuAlaG luValValGl uLysCysAla PheSerAspA

ACACGGTGAT CGTTAATGTG CAGGGTGATG AACCGATGAT     440
          spThrValIl eValAsnVal GlnGlyAspG luProMetIl

CCCTGCGACA ATCATTCGTC AGGTTGCTGA TAACCTCGCT     480
          eProAlaThr IleIleArgG lnValAlaAs pAsnLeuAla
```

FIG.12A

```
          10         20         30         40
    1234567890 1234567890 1234567890 1234567890
    CAGCGTCAGG TGGGTATGAC GACTCTGGCG GTGCCAATCC    520
    GlnArgGlnV alGlyMetTh rThrLeuAla ValProIleH

ACAATGCGGA AGAAGCGTTT AACCCGAATG CGGTGAAAGT    560
    isAsnAlaGl uGluAlaPhe AsnProAsnA laValLysVa

GGTTCTCGAC GCTGAAGGGT ATGCACTGTA CTTCTCTCGC    600
    lValLeuAsp AlaGluGlyT yrAlaLeuTy rPheSerArg

GCCACCATTC CTTGGGATCG TGATCGTTTT GCAGAAGGCC    640
    AlaThrIleP roTrpAspAr gAspArgPhe AlaGluGlyL

TTGAAACCGT TGGCGATAAC TTCCTGCGTC ATCTTGGTAT    680
    euGluThrVa lGlyAspAsn PheLeuArgH isLeuGlyIl

TTATGGCTAC CGTGCAGGCT TTATCCGTCG TTACGTCAAC    720
    eTyrGlyTyr ArgAlaGlyP heIleArgAr gTyrValAsn

TGGCAGCCAA GTCCGTTAGA ACACATCGAA ATGTTAGAGC    760
    TrpGlnProS erProLeuGl uHisIleGlu MetLeuGluG

AGCTTCGTGT TCTGTGGTAC GGCGAAAAAA TCCATGTTGC    800
    lnLeuArgVa lLeuTrpTyr GlyGluLysI leHisValAl

TGTTGCTCAG GAAGTTCCTG GCACAGGTGT GGATACCCCT    840
    aValAlaGln GluValProG lyThrGlyVa lAspThrPro

GAAGATCTCG ACCCGTCGAC GAATTCGAGC TCGGTACCCG    880
    GluAspLeuA spProSerTh rAsnSerSer SerValProG

GGGATCCTCT AGACTGCAGG CATGCTAAGT AAGTAGATCT    920
    lyAspProLe uAspCysArg HisAlaLys
```

EMBEDDED EXPRESSION OF INSOLUBLE HETEROLOGOUS PROTEINS

TECHNICAL FIELD

The present invention relates to methods for the production, by microbial host cells, of heterologous proteins. More particularly, the invention relates to the expression of such proteins in the form of fusion proteins in which the proteins of interest are embedded, and also to DNA constructs, plasmid vectors and transformed host cells useful for making the same.

BACKGROUND OF THE INVENTION

Although it is well-known to express both prokaryotic and eukaryotic non-native ("heterologous") proteins in microbial hosts, there are a number of technical difficulties which must be overcome in expressing a protein; these include (i) attaining a sufficient level of expression, (ii) obtaining the protein in a form which is readily isolated and purified, and (iii) ensuring that the protein is fully expressed and not truncated as by incomplete translation or by subsequent degradation. One approach has been to co-express the protein of interest with another "carrier" protein by joining the genes for each; the resulting fusion proteins usually contain the two gene products covalently linked together, either directly or through a short linking segment.

A particularly favorable expression system has been described in U.S. Pat. No. 5,124,255, which patent is expressly incorporated herein by reference. In that patent, fusion proteins are disclosed which utilize as a carrier protein the *Escherichia coli* enzyme CKS (CMP-KDO synthetase, or CTP:CMP-3-deoxy-D-manno-octulosonate cytidylyl transferase). That carrier permits the expression at high levels of the desired fusion proteins, in which the protein of interest is encoded for by DNA which is positioned at the 3' end of the carrier gene. However, it can occur in this and other expression systems that the fusion product is not easily separated from closely-related expression products or cellular contaminants of similar molecular weight. Also, it may happen that the protein of interest, which typically is at the C-terminus of the fusion protein, is truncated rather than being full-length.

These difficulties must be overcome when, for example, the protein of interest is an epitope or combination of epitopes which is to be used in a diagnostic immunoassay, and consequently must be fully-expressed and purifiable. It therefore remains an object of the present invention to develop improved expression systems which permit the reliable expression of a wide variety of complete heterologous proteins, and furthermore which facilitate the purification of such proteins.

SUMMARY OF THE INVENTION

It has now been found that intact heterologous proteins may be readily expressed as fusion proteins in which the heterologous protein is embedded in, and not appended to, the carrier which acts as fusion partner. This approach simplifies purification of the protein from contaminating host cell proteins and from contaminating recombinant protein truncation products.

Accordingly, in one aspect of the invention is disclosed a method for expressing a heterologous protein in a prokaryotic host cell, comprising the steps of (a) providing a DNA vector having (1) a control region operatively linked to a first genetic element encoding a carrier protein capable of expression in the host cell, and (2) a second genetic element encoding the heterologous protein, the second element being embedded within the first element such that the first and second elements are contiguous and in the same reading frame; (b) transforming the host cell with the DNA vector; and (c) expressing a fusion protein of the heterologous protein and the carrier protein, wherein the heterologous protein is joined at its N-terminus to a first domain of the carrier protein and at its C-terminus to a second domain of the carrier protein.

In a second aspect of the present invention are disclosed heterologous proteins expressed according to the expression method of the invention. Fusion proteins comprising a heterologous protein, which are made according to the above method, are similarly disclosed.

In another aspect of the present invention is disclosed a method for confirming the intact expression of a heterologous protein, comprising the steps of (a) expressing the heterologous protein as a fusion protein according to the expression method of the invention; (b) isolating the fusion protein; and (c) exposing the fusion protein to means for detecting the presence of a portion of the second domain of the carrier protein.

In a further aspect of the present invention are disclosed DNA constructs for insertion into a plasmid vector, comprising (a) a control region operatively linked to a first genetic element encoding a carrier protein capable of expression in a host cell, and (b) a second genetic element encoding a heterologous protein, the second element being embedded within the first element such that the first and second elements are contiguous and in the same reading frame.

In still another aspect of the present invention are disclosed plasmid vectors comprising a DNA construct of the invention, as well as host cells transformed therewith.

BRIEF DESCRIPTION OF THE DRAWINGS

The following description of the present invention will be more readily appreciated in connection with the appended drawings, in which:

FIG. 12 is the DNA sequence (SEQ ID NO:5) of nucleotides 1-920, and the corresponding amino acid sequence of amino acids 1-260 SEQ ID NO:5), of plasmid pJO200.

DETAILED DESCRIPTION OF THE INVENTION

Figure 1:
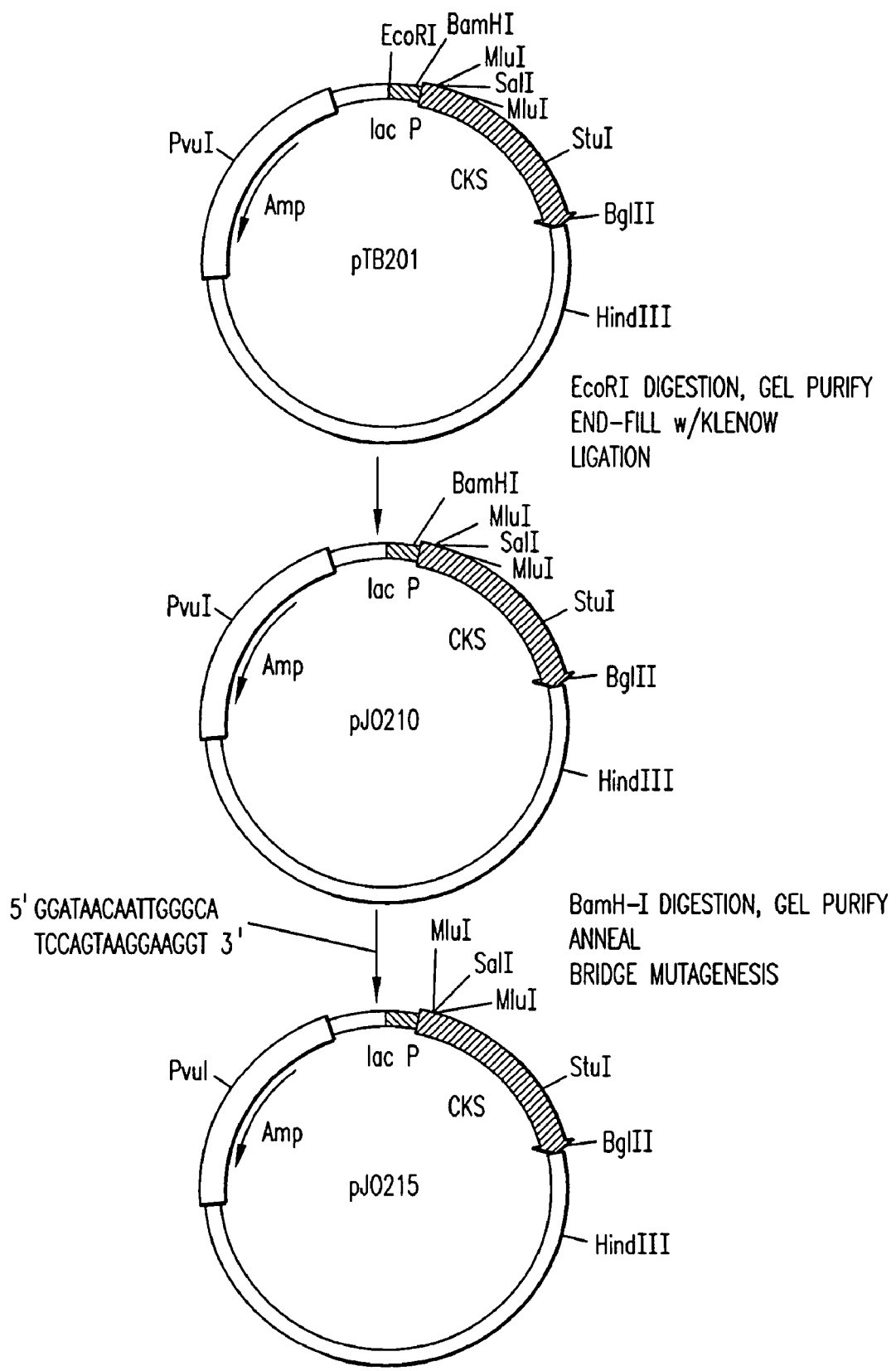
FIG. 1 is a schematic representation of the construction of plasmids pJO210 and JO215 and the elimination of restriction sites EcoRI and BamHI.

Accordingly, in one aspect of the invention is disclosed a method for expressing a heterologous protein in a prokaryotic host cell, comprising the steps of (a) providing a DNA vector having (1) a control region operatively linked to a first genetic element encoding a carrier protein capable of expression in the host cell, and (2) a second genetic element encoding the heterologous protein, the second element being embedded within the first element such that the first and second elements are contiguous and in the same reading frame; (b) transforming the host cell with the DNA vector; and (c) expressing a fusion protein of the heterologous protein and the carrier protein, wherein the heterologous protein is joined at its N-terminus to a first domain of the carrier protein and at its C-terminus to a second domain of the carrier protein.

In the method of expression of the present invention, the heterologous protein may be any protein capable of expression in the host cell and sufficiently benign that expression will not significantly harm or inhibit the growth of the host. Suitable heterologous proteins may be of bacterial, fungal, yeast, viral, protozoan or other source (including zoonosis-causing organisms such as *Trypanosoma cruzi* or *Toxoplasma gondii*), although bacterial and viral proteins are preferred.

Especially preferred are viral proteins, and in particular proteins which are derived from the human cytomegalovirus (HCMV), a pathogen of considerable clinical significance; such proteins are important in the diagnosis of HCMV infection by their use as assay targets in the determination of the presence or absence of HCMV-specific immunoglobulins. Included among the representative HCMV proteins which may be expressed by the method of the present invention, and which contain epitopes readily identified by human immunoglobulins, are pp38 (a 38 kD assembly protein), pp65 (a 65 kD major matrix protein), pp52 (a 52kD non-structural DNA-binding protein), pp150 (a 150 kD structural phosphoprotein); of these, HCMV proteins pp38 and pp65 are preferred. Also preferred are heterologous proteins which comprise an immunogenic portion of an epitope selected from among HCMV epitopes H10, F3 and A1C2; these epitopes have been found to provide a sensitive and specific means of assaying for immunoglobulins directed to HCMV.

Representative control regions suitable for use in the above method include those comprising a prokaryotic promoter and a prokaryotic ribosomal binding site, and especially those wherein the control region comprises a lac operon. However, depending on the host cell used, other control regions well-known in the art may also be employed.

A representative carrier protein (fusion partner with which the heterologous gene is fused and co-expressed) is one derived from CKS protein, although it is expected that the embedded expression method of the present invention will find broad application with other carrier proteins as well, including but not limited to beta-galactosidase, glutathione-S-transferase, and maltose binding protein. When CKS is used, a particularly preferred embodiment of the DNA vector used in the above method is one in which the heterologous protein is positioned between a first domain of the carrier protein comprising a portion of amino acids 1 through 171 of CKS, and a second domain of the carrier protein comprising a portion of amino acids 171 through 260 of CKS. (As described below, what is referred to as CKS protein may include both the first 240 amino acids of the original kdsB gene followed by an additional 20 amino acids at the end of the CKS gene encoded for by a polylinker DNA sequence.)

Consequently, preferred fusion proteins of the present invention include those having the sequence CKS*-CMV*-Thr-Arg-CKS**, wherein (a) CKS* is a portion of amino acids 1 through 171 of CKS; (b) CMV* is a portion of an HCMV protein; and (c) CKS** is a portion of amino acids 171 through 260 of CKS. Of these, especially preferred are fusion proteins wherein CMV* is selected from among portions of the HCMV proteins pp38, pp52, pp65 and pp150, and particularly from among immunogenic portions of HCMV proteins pp38 or pp65 or immunogenic portions of the HCMV epitopes H10, F3 and A1C2. Particular examples of such fusion proteins are those in which CMV* is selected from among (a) A1C2F3-Leu-Gln-H10; (b) pp65(297-510aa); (c) pp65(297-510aa)-STOP, where STOP is a stop codon; and (d) pp38(117-373aa).

In the method of the present invention by which intact expression of an heterologous protein is confirmed, isolation of the fusion protein may be carried out by known separatory methods such as differential migration in an electrophoretic gel of the fusion protein with respect to other expression products (such as incomplete or truncated fusion products) or cellular components. (It should be noted that by "isolation" is meant only that various molecular species are separated or resolved, and not that the desired fusion protein is isolated in pure form.) After isolation, any suitable detection means for establishing the presence of some or all of the carrier protein domains which flank the heterologous protein may be used. Preferred detection means comprise an immunoglobulin which is immunoreactive with an epitope contained in the first or second domain of the carrier protein. A particularly useful method for both isolating the fusion protein and exposing the protein to such detection means is the Western blotting procedure.

The DNA constructs of the present invention are those corresponding to the above method and fusion protein. Consequently, preferred constructs are those which comprise sequences encoding the preferred heterologous proteins, epitopes, control regions, carrier proteins and juxtaposition of fusion protein elements described above. When incorporated into the plasmid vectors of the invention, preferred vectors include those selected from among (a) pCMV-27; (b) pCMV-28; (c) pCMV-28STOP; and (d) pCMV-29.

The present invention in its various aspects may be carried out using recombinant methodology well-known in the art. For example, conventional expression of heterologous proteins using the CKS protein as a carrier is described in the above-mentioned U.S. Pat. No. 5,124,255. Related procedures are also described in detail in U.S. Pat. Nos. 5,312,737 and 5,322,769 and the references cited therein.

The expression methods, confirmatory methods, fusion proteins, DNA constructs, plasmid vectors and transformed host cells of the present invention will be better understood in connection with the following examples, which are intended as an illustration of and not a limitation upon the scope of the invention. Both below and throughout the specification, it is intended that citations to the literature are expressly incorporated by reference.

Example 1

General Methodology

Materials and Sources

Restriction enzymes, T4 DNA ligase, calf intestinal alkaline phosphatase (CIAP), polynucleotide kinase, and the Klenow fragment of DNA Polymerase I were purchased from New England Biolabs, Inc. (Beverly, Mass.) or from Boehringer Mannheim Corp. (Indianapolis, Ind.). DNaseI and aprotinin were purchased from Boehringer Mannheim Corp.

DNA and protein molecular weight standards, Daiichi precast gradient polyacrylamide gels, and Semi-Dry Blotting System with buffers were obtained from Integrated Separation Systems, Inc. (Natick, Mass.).

Isopropyl-β-D-thiogalactoside (IPTG), acrylamide, N-N'-methylene-bis-acrylamide, N,N,N',N'-tetramethylethylenediamine (TEMED), 4-chloro-1-napththol, Coomassie™ Brilliant Blue R250, Triton X-100™ and sodium dodecylsulfate (SDS) were purchased from BioRad Laboratories (Richmond, Calif.).

Horseradish peroxidase (HRPO)—labelled antibodies were purchased from Kirkegaard & Perry Laboratories, Inc. (Gaithersburg, Md.). EPICURIAN Coli™ XL-1 BLUE (recA1 endA1 gyrA96 thi-1 hsdR17 supE44 relA1 lac [F' proAB lacIq ZΔM15 Tn10 (Tet$^r$)]) supercompetent $E.$ $coli$ cells, DNA isolation kit, RNA isolation kit, and ZAP™-cDNA Synthesis kit were obtained from Stratagene Cloning Systems, Inc. (La Jolla, Calif.).

GeneAmp™ reagent kit and AmpliTaq™ DNA Polymerase were purchased from Perkin-Elmer Cetus (Norwalk, Conn.). Deoxynucleotide triphosphates used in general procedures were from the GeneAmp™ reagent kit.

Supported nitrocellulose membrane was purchased from Schleicher & Schuell (Keene, N.H.).

Nucleotide kit for DNA sequencing with Sequenase™ and 7-deaza-dGTP and Sequenase™ version 2.0 DNA Polymerase were obtained from U.S. Biochemical Corp. (Cleveland, Ohio).

PolyA$^+$ mRNA purification kit was purchased from Pharmacia LKB Biotechnology, Inc. (Piscataway, N.J.).

Luria Broth plates with ampicillin (LBamp plates) were purchased from Micro Diagnostics, Inc. (Lombard, Ill.).

OPTI-MEM™ Medium, fetal calf serum, phosphate-buffered saline, competent $E.$ $coli$ DH5α (F$^-$Ø80dlacZΔM15 Δ(lacZYA-argF)U169 deoR recA1 endA1 phoA hsdR17($r_K^-$, $m_K^+$) supE44 λ$^-$ thi-1 gyrA96 relA1), and ultraPURE™ agarose were purchased from GIBCO BRL, Inc. (Grand Island, N.Y.).

Bacto-Tryptone, Bacto-Yeast Extract, and Bacto-Agar were obtained from Difco Laboratories (Detroit, Mich.).

NZY™ Broth was purchased from Becton Dickinson Microbiology Systems (Cockeysville, Md.).

Salmon sperm DNA, lysozyme, ampicillin, N-lauroyl sarcosine, thimerosal, buffers, casein acid hydrolysate, TWEEN 20™ (polyoxyethylenesorbitan monolaurate), diethylpyrocarbonate (DEPC), phenylmethylsulfonylfluoride (PMSF), bovine serum albumin (BSA), urea, glycerol, EDTA, sodium deoxycholate and inorganic salts were purchased from Sigma Chemical Co. (Saint Louis, Mo.).

Polystyrene microparticles were purchased from Polysciences, Inc. (Warrington, Pa.).

Hydrogen Peroxide ($H_2O_2$) was purchased from Mallinkrodt (Paris, Ky.).

Methanol was purchased form EM Science (Gibbstown, N.J.).

Media, Buffers and General Reagents

"Superbroth II" contained 11.25 g/L tryptone, 22.5 g/L yeast extract, 11.4 g/L potassium phosphate dibasic, 1.7 g/L potassium phosphate monobasic, 10 mL/L glycerol, adjusted pH to 7.2 with sodium hydroxide.

"Tris-buffered saline" or "TBS" consisted of 20 mM Tris, 500 mM NaCl at pH 7.5.

"Tris-buffered saline TWEEN 20™" or "TBST" consisted of TBS plus 0.05% TWEEN 20™.

"Membrane blocking solution" consisted of 1% Bovine Serum Albumin (BSA), 1% casein acid hydrolysate, and 0.05% TWEEN 20™ in TBS.

"Rubazyme specimen dilution buffer" or "Rubazyme SDB" consisted of 100 mM Tris at pH 7.5 with 135 mM NaCl, 10 mM EDTA, 0.2% TWEEN 20 ™, 0.01% thimerosal and 4% bovine calf serum.

"Rubazyme conjugate diluent dilution buffer" consisted of 100 mM Trisat pH 7.5 with 135 mM NaCl, 0.01% thimerosal and 10% bovine calf serum.

"HRPO color development solution" consisted of 0.06% 4-chloro-1-napththol, 0.02% $H_2O_2$ and 0.2% methanol in TBS.

"SDS-PAGE loading buffer" consisted of 62 mM Tris at pH 6.8 with 2% SDS, 10% glycerol, 5% β-mercaptoethanol and 0.1% bromophenol blue.

"TE buffer" consisted of 10 mM Tris and 1 mM EDTA at pH 8.0.

"TEM lysis buffer" consisted of 50 mM Tris, 10 mM EDTA and 20 mM magnesium chloride at pH 8.5.

"PTE buffer" consisted of 50 mM Tris and 10 mM EDTA at pH 8.5.

Virus Propagation and Preparation of cDNA

The HCMV AD169 strain or the Towne strain were used interchangeably and were propagated in human fibroblasts grown in OPTI-MEM™ Medium supplemented with 5% fetal calf serum. HCMV AD169 and the HCMV genome is described in the publications of Chee et al., $Curr.$ $Top.$ $Microbiol.$ $Immuno.$ 154:125 (1990) and Bankier et al., $DNA$ $Seq.$ 2:1 (1991), which disclosures are incorporated herein by reference.

Six (6) days post-infection, the CMV-infected fibroblast cells were harvested by centrifugation, washed with PBS, and homogenized with a glass-Teflon™ homogenizer. Total viral DNA was isolated as described in Mocarski et al., $Proc.$ $Nat.$ $Acad.$ $Sci.$ 82:1266 (1985). Total RNA was isolated from the homogenized cells using the RNA Isolation Kit (Stratagene Cloning Systems) and polyA$^+$ RNA was isolated using a mRNA Isolation Kit (Pharmacia Biotech). HCMV cDNA was synthesized from the purified viral mRNA using a ZAP-cDNA™ Synthesis Kit (Stratagene Cloning Systems).

General Methods

All enzyme digestions of DNA were performed according to suppliers' instructions. At least 5 units of enzyme were used per microgram of DNA, and sufficient incubation time was allowed for complete digestion of DNA. Supplier protocols were followed for the various kits used in manipulation of DNA and RNA, for polymerase chain reaction (PCR) DNA synthesis and for DNA sequencing. Standard procedures were used for miniprep and large scale preparation of plasmid DNA from *E. coli*, preparation of phage lysate DNA from *E. coli* cells infected with phage λ, preparation of *E. coli* lysates for the absorption of anti-*E. coli* antibodies, phenol-chloroform extraction and ethanol precipitation of DNA, restriction analysis of DNA on agarose gels, purification of DNA fragments from agarose and polyacrylamide gels, filling the recessed 3' termini created by digestion of DNA with restriction enzymes using the Klenow fragment of DNA Polymerase I, ligation of DNA fragments with T4 DNA ligase, and for preparation of competent TB1 cells (F⁻ ara d(lac-proAB) rpsL Ø80dlacZΔM15 hsdR17) (Maniatis et al., *Molecular Cloning: A Laboratory Manual*, 2nd ed. (Cold Spring Harbor Laboratory Press, New York, 1989).

DNA fragments for cloning into plasmids that were generated by PCR amplification, were extracted with phenol-chloroform and precipitated with ethanol prior to restriction enzyme digestion of the PCR reaction mixture. Oligonucleotides for PCR and DNA sequencing were synthesized on an Applied Biosystems Oligonucleotide Synthesizer, model 380B or 394, per the manufacturer's protocol.

Mouse monoclonal antibodies directed against the HCMV proteins A1C2F3 (from the viral gene UL32), H10 (UL44) and pp65 (UL83) were obtained by immunization of mice with purified rpMB34 (lacZ-A1C2F3), purified rpROSH10 (lacZ-H10), and purified rpCMV-9 (CKS-pp65(297-510aa)), respectively. Mouse monoclonal antibody directed against the CKS protein was obtained by immunization of mice with purified rpHCV-23 (CKS-BCD), described in Published International Application No. WO93/04088 by Dailey et al. The proteins used for immunization were approximately 90% pure as determined by SDS-PAGE. The procedure for the immunization of mice, cell fusion, screening and cloning of monoclonal antibodies, and characterization of monoclonal antibodies were as described in Published International Application No. WO92/08738 by Mehta et al.

Example 2

Construction of CKS Expression Vector pJO200

Figure 2:
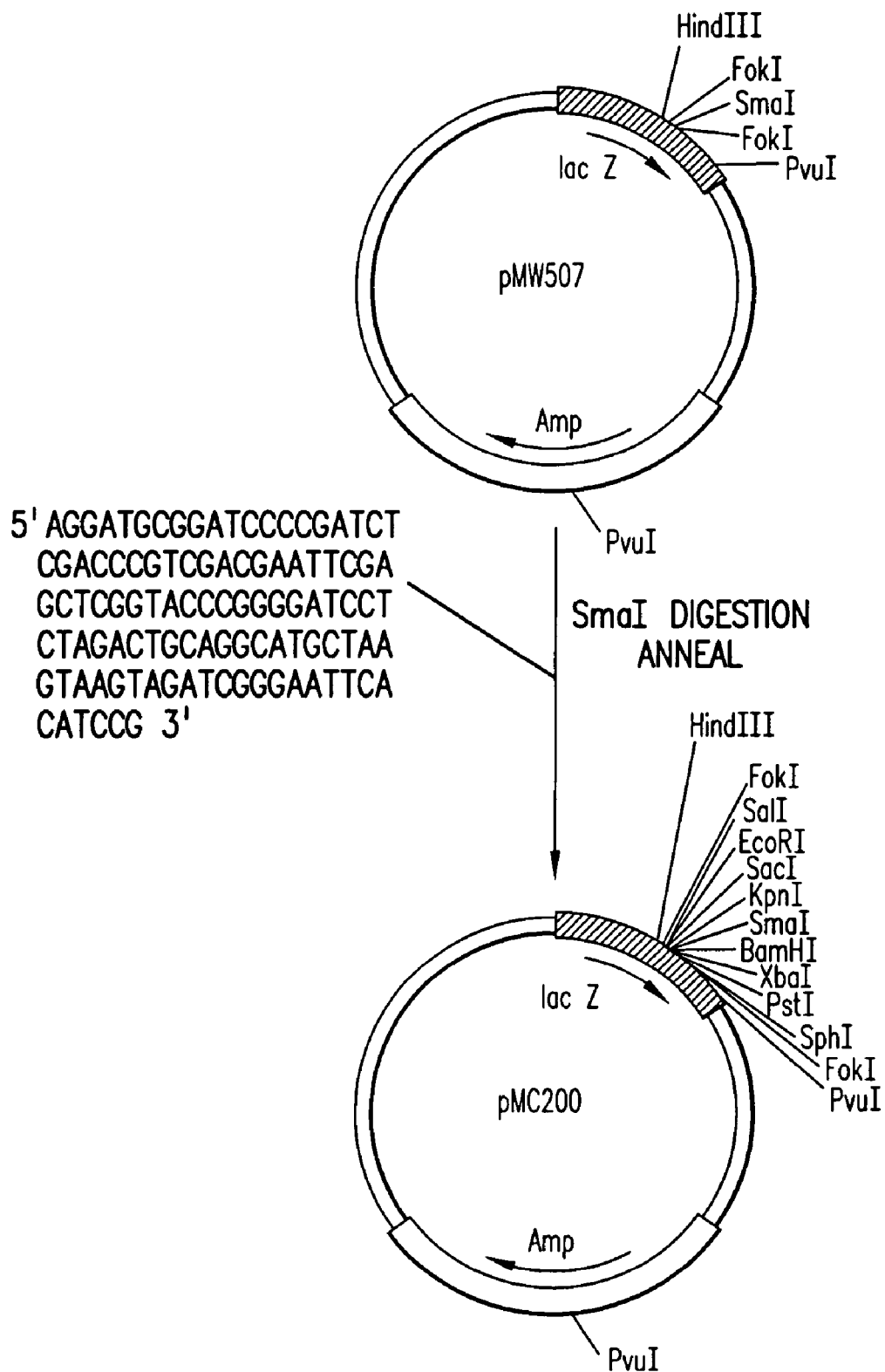
FIG. 2 is a schematic representation of the construction of plasmid pMC200 including the use of the oligonucleotide having the sequence of SEQ ID NO:2.
Figure 3:
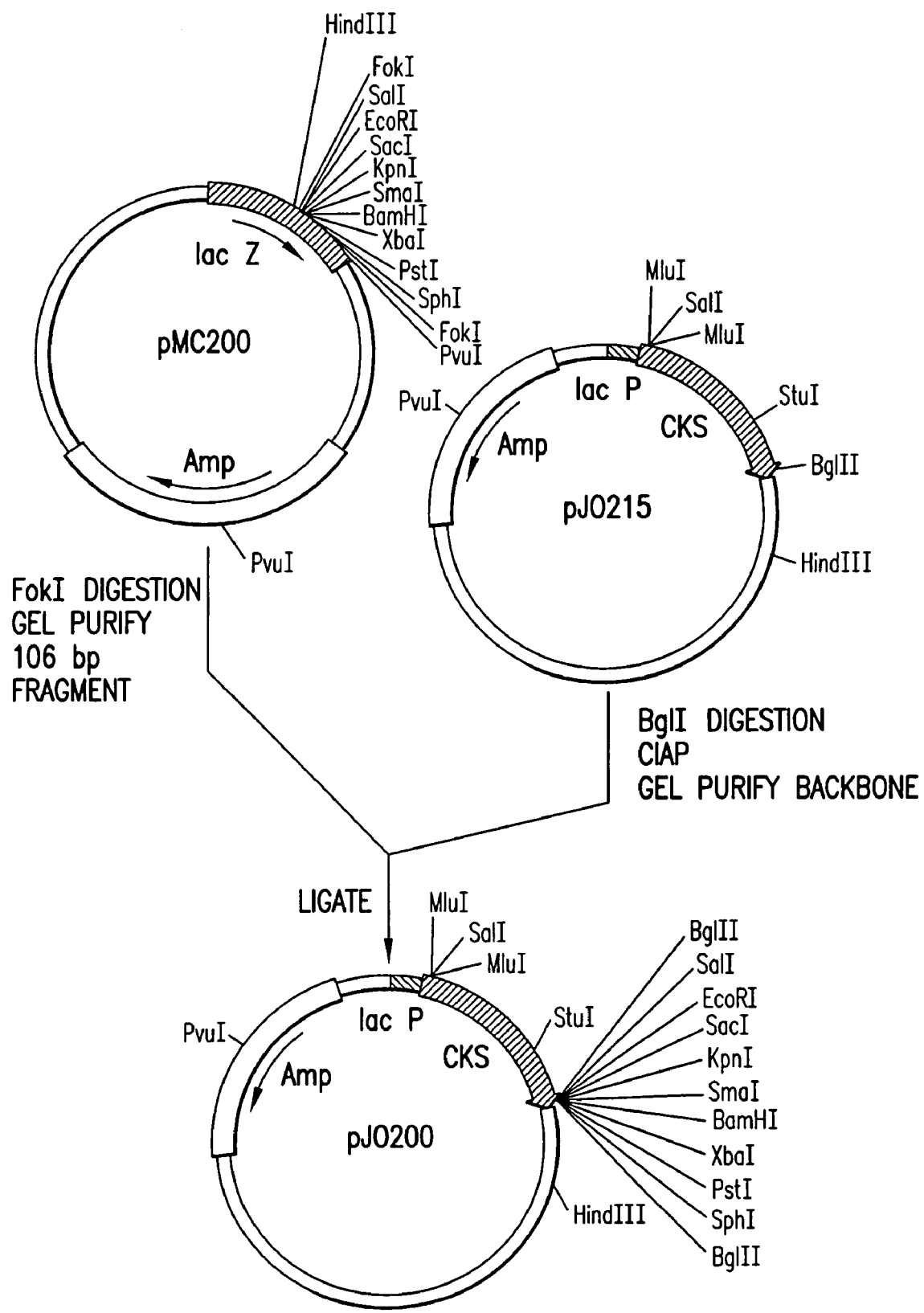
FIG. 3 is a schematic representation of the construction of plasmid pJO200.

As represented in FIGS. 1-3, the pJO200 vector was constructed in three steps starting with the plasmid pTB201, described in Bolling and Mandecki, *Bio/Techniques* 8:488 (1990). The construction of the CKS expression vector pJO200 allowed for the fusion of recombinant proteins to the *E. coli* CMP-KDO synthetase (CKS) protein. The DNA gene sequence which encodes for the structural protein CKS (also known as the kdsB gene) is published in Goldman et al., *J. Biol. Chem.* 261:15831 (1986). The amino acid sequence of CKS includes 248 amino acid (aa) residues, and is described in the same article.

The construction plan for plasmid pJO200 involved the removal of two restriction enzyme sites (EcoRI and BamHI) and the addition of a multi-cloning site at the 3' end of the CKS gene. This was done to facilitate the later cloning of CMV genes encoding for CMV protein antigens at the 3' end of CKS. The completed vector contained DNA encoding the sequence of the first 240 amino acids from the original kdsB gene followed by an additional 20 amino acids encoded for by the polylinker DNA sequence, for a total of 260 amino acids.

Step A: Construction of pJO210

The plasmid pJO210 is a derivative of the CKS expression vector, pTB201 (FIG. 1). This plasmid was constructed by removing a single EcoRI site present in pTB201 located upstream from the promoter for the CKS gene. Large scale plasmid DNA (pTB201) was isolated from TB1 cells using general methods. The DNA was digested to completion with EcoRI, and purified on a polyacrylamide gel. The purified pTB201/EcoRI fragment then was treated with the Klenow fragment of DNA Polymerase I in the presence of deoxynucleotide triphosphates. This enzyme filled in the recessed 3' termini produced after the EcoRI digestion, leaving blunt ends. The DNA was extracted with phenol/chloroform after treatment with the Klenow fragment, ethanol precipitated, and re-suspended in T4 DNA ligase buffer and finally ligated at room temperature with T4 DNA ligase for 4 hours. The ligation mixture was transformed into competent TB1 cells. A miniprep of DNA was prepared from the transformants and the DNA was screened for the loss of the EcoRI site. Plasmid pJO210 was isolated, having lost the EcoRI site of plasmid pTB201.

Step B: Construction of pJO215

The plasmid pJO215 is a derivative of the plasmid pJO210 (FIG. 1). This plasmid was constructed by removing a single BamHI site of pJO210, located in the promoter for the CKS gene, by using the bridge mutagenesis procedure of Mandecki, *Proc. Nat. Acad. Sci.* 83:7177 (1986). Plasmid DNA (pJO210) from TB1 cells was isolated using general methods. The DNA was digested with BamHI to completion and purified on an acrylamide gel. The purified pJO210/BamHI fragment then was mixed with a mutagenic oligonucleotide which was complementary to one of the DNA strands of pJO210 in the region of the plasmid spanning the BamHI site and had the sequence [SEQ ID NO: 1]

```
5'GGATAACAAT TGGGCATCCA GTAAGGAGGT 3'
```

This oligonucleotide contained a single G-to-C base change (at nucleotide #15, underlined above) which removed the BamHI site when incorporated into plasmid pJO210.

After mixing the mutagenic oligonucleotide with pJO210/BamHI, the mixture was boiled for 3 minutes, cooled to room temperature for 5 minutes, and then transformed into competent TB1 cells. Miniprep DNA was prepared from the transformants and screened for the loss of the BamHI site. Plasmid pJO215 was isolated, having lost the BamHI site of plasmid pJO210.

Step C: Construction of pMC200

The plasmid pMC200 (FIG. 2) is a derivative of plasmid pMW507, described in Mandecki and Bolling, *Gene* 68:101 (1988). This plasmid was constructed by cloning a synthetic oligonucleotide containing a multi-cloning site into pMW507 using the FokI method of gene synthesis described by Mandecki and Bolling.

Large scale plasmid pMW507 DNA was isolated from TB1 cells using general methods. The DNA was digested to completion with SmaI and then mixed with an oligonucleotide having the sequence [SEQ ID NO:2]

```
5'AGGATGCGGA TCCCCGATCT CGACCCGTCG ACGAATTCGA
  GCTCGGTACC CGGGGATCCT CTAGACTGCA GGCATGCTAA
  GTAAGTAGAT CGGGAATTCA CATCCG 3'
``` which contained FokI arms at the end and several restriction enzyme sites.

The multi-cloning site nucleotide included the following restriction sites and sequences: 5' FokI arm—BglII sticky end-SalI/AccI/HincII-EcoRI-SstI-KpnI-SmaI/XmaI-BamHI-XbaI-PstI-SphI-stop codons-BglII sticky end-FokI arm 3'. The oligonucleotide was mixed with pMW507/SmaI and the mixture was boiled for 3 minutes, cooled to room temperature for 5 minutes, and then transformed into competent TB1 cells. Miniprep DNA was prepared from the transformants and screened for the presence of the multi-cloning site. Plasmid pMC200 contained the multi-cloning site insertion into pMW507 as was confirmed by DNA sequencing.

Step D: Construction of pJO200

The plasmid pJO200 is a derivative of plasmid pJO215 (FIG. 3). Plasmid pJO200 was constructed by removing the multi-cloning site from pMC200 and cloning this site at the 3' end of the CKS gene in pJO215.

Large scale plasmid DNA (both pMC200 and pJO215) was isolated from TB1 cells using general methods. Plasmid pJO215 DNA was digested to completion with BglII and then treated with calf intestinal alkaline phosphatase (CIAP) to prevent recircularization of the plasmid during the ligation reaction. Plasmid pMC200 DNA was digested with FokI. Digestion of plasmid pMC200 with FokI released the multi-cloning site DNA from the plasmid. This DNA contained BglII sticky ends, which could readily ligate into pJO215 DNA after it was digested with BglII. Plasmid pJO215/BglII/CIAP and the multi-cloning site released from pMC200/FokI (106 base pairs) were purified by polyacrylamide gel electrophoresis.

Plasmid pJO215/BglII/CIAP and the multi-cloning site released from pMC200/FokI were mixed and ligated at 16° C. with T4 DNA ligase overnight. The next day, the ligation mixture was transformed into competent TB1 cells. Miniprep DNA was prepared from the transformants and screened for the presence of the multi-cloning site in the correct orientation at the BglII site. Plasmid pJO200 contained the multi-cloning site in the correct orientation. The DNA sequence of the multi-cloning site in pJO200 at the BglII site was confirmed by DNA sequencing.

Example 3

Construction of the lacZ-A1C2F3 Expression Vector pMB34

The plasmid pMB34 contained HCMV sequences and was a derivative of the lacZ expression vector pROS described in Ellinger et al., *J. Clin. Micro.* 27: 971 (1989). The pROS vector contained a truncated form of the lacZ gene (1-375 amino acids) with a polylinker cloning site located downstream of the lacZ gene. The pMB34 plasmid was constructed in two steps. The first step required joining two regions of ppUL32, which encodes a basic HCMV phosphoprotein of 150 kD (pp150), then joining this HCMV fusion to the 3' end of the lacZ gene in pROS.

Step A: Construction of pMB28: lacZ-A1C2

Figure 4:
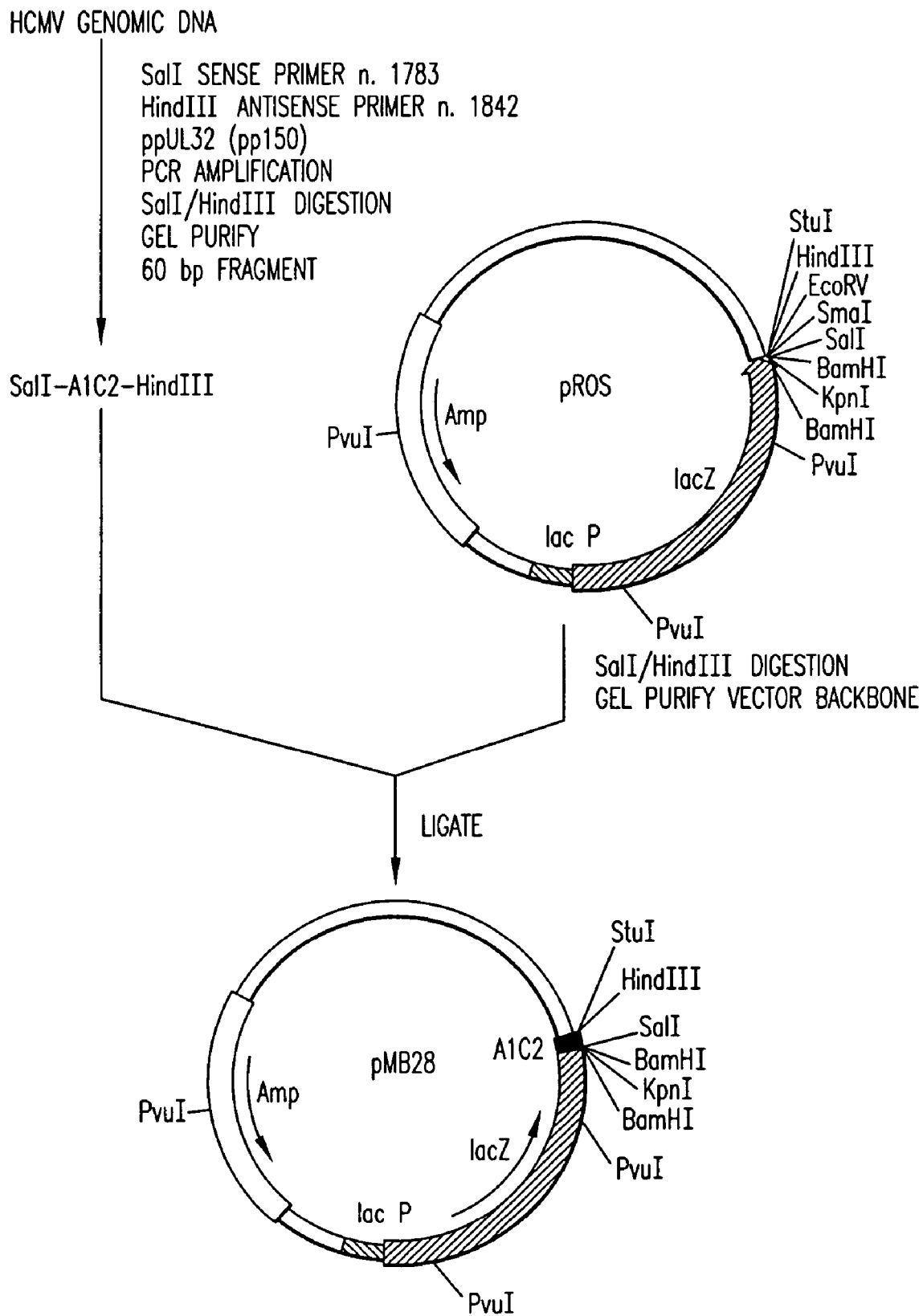
FIG. 4 is a schematic representation of the construction of plasmid pMB28:lacZ-A1C2.

The plasmid pMB28, a derivative of plasmid pROS (FIG. 4), was constructed by cloning a DNA fragment containing HCMV-A1C2 into the polylinker region of pROS. HCMV-A1C2 was obtained by PCR amplification of HCMV genomic DNA from the region of ppUL32 gene encoding amino acids 595-614 of pp150 (nucleotides 1783-1842 of ppUL32, where nucleotides 1 and 3144 correspond to nucleotides 42993 and 39850, respectively, of the complementary strand of the AD169 DNA sequence as reported in Chee et al. (1990) and Bankier et al. (1991).

Large scale plasmid DNA (pROS) was isolated from DH5α cells using general methods. Plasmid pROS was digested with SalI and HindIII and the vector backbone was purified on an agarose gel. A sense primer, starting at nucleotide 1783 of ppUL32 containing a SalI site, and an antisense primer, starting at nucleotide 1842 of ppUL32 containing a HindIII site, were synthesized and added to a PCR reaction mixture containing genomic HCMV DNA. After PCR amplification, the reaction mixture was digested with SalI and HindIII, and the 60 base pair fragment that contained the epitope known as A1C2 (nucleotides 1783-1842 of ppUL32) was purified on an agarose gel. This purified fragment then was ligated to purified pROS/SalI/HindIII by incubation overnight at 16° C. The ligation mixture was transformed the next day into competent DH5α cells. Miniprep DNA was prepared from the transformants, and the transformants was screened for the presence of the 60 base pair fragment in pROS at the end of the lacZ gene. Plasmid pMB28 contained the A1C2 fragment. The DNA sequence of A1C2 in pMB28 was confirmed by DNA sequencing, and the A1C2 coding region was determined to be in-frame with the lacZ coding sequence.

Step B: Construction of pMB34: lacZ-A1C2F3

Figure 5:
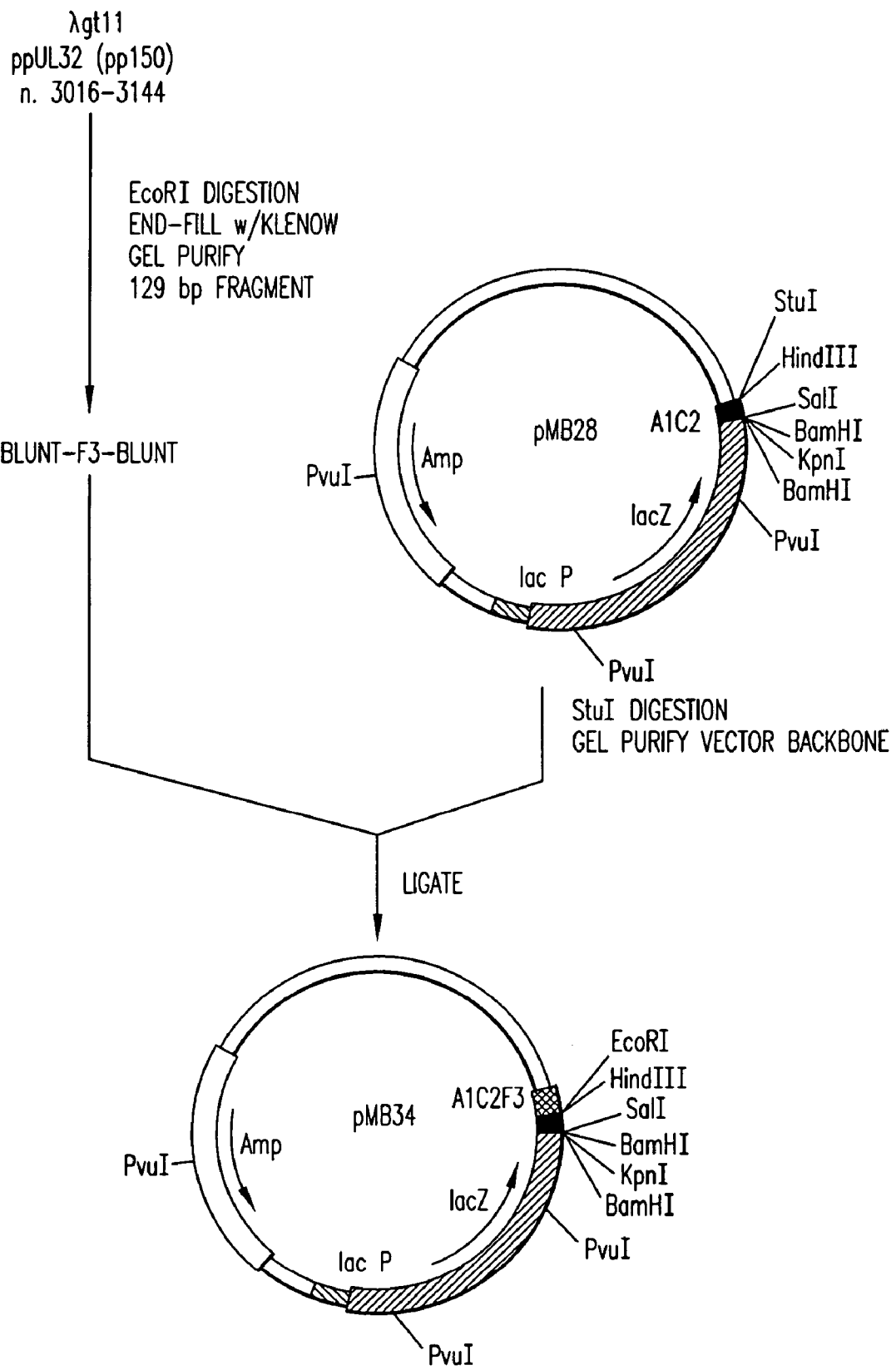
FIG. 5 is a schematic representation of the construction of plasmid pMB34:lacZ-A1C2F3.

The plasmid pMB34, a derivative of plasmid pMB28 (FIG. 5), was constructed by cloning a DNA fragment that contained the HCMV-F3 epitope into the polylinker region of pMB28, just downstream of the A1C2 DNA sequence. The DNA fragment that contained the HCMV-F3 epitope was obtained from a λgt11 subclone of ppUL32 encoding amino acids 1006-1048 of pp150 (nucleotides 3016-3144) and was from the λgt11 library described by Mocarski et al. in *Proc. Nat. Acad. Sci.* 82:1266 (1985).

Large scale plasmid DNA (pMB28) was isolated from DH5α cells using general methods. Phage lysate DNA was prepared from the phage λgt11 clone λ-F3 using general methods. Plasmid pMB28 was digested with StuI and the vector backbone with blunt-ends was purified on an agarose gel. Phage λ-F3 DNA was digested with EcoRI and the recessed 3' termini were filled in with the Klenow fragment of DNA Polymerase I, leaving blunt ends. The blunt-ended 129 base pair λ-F3 fragment was purified on an agarose gel and then blunt-end ligated to pMB28/StuI overnight at 16° C. The ligation mixture was transformed the next day into competent DH5α cells. Miniprep DNA was prepared from the transformants and the transformants were screened for the presence of the 129 base pair fragment in pMB28 at the end of the lacZ gene in the correct orientation. Plasmid pMB34 contained the F3 fragment in the correct orientation. The DNA sequence of F3 in plasmid pMB34 was confirmed by DNA sequencing. The F3 coding region was in-frame with the lacZ-A1C2 coding sequence. The coding region of the lacZ-A1C2F3 construct in pMB34 contained a bridge of 5 amino acids having the sequence [SEQ ID NO:3]

Lys-Leu-Gln-Glu-Phe (or K-L-Q-E-F) between A1C2 and F3, resulting in a construct which was designated "lacZ(1-375aa)-A1C2(595-614aa, pp150)-K-L-Q-E-F-F3(1006-1048aa, pp150)". The entire construct, including the pentapeptide insert, is herein referred to as "A1C2F3".

Example 4

Construction of lacZ-pp38(106-373aa) Expression Vector pMB38

Figure 6:
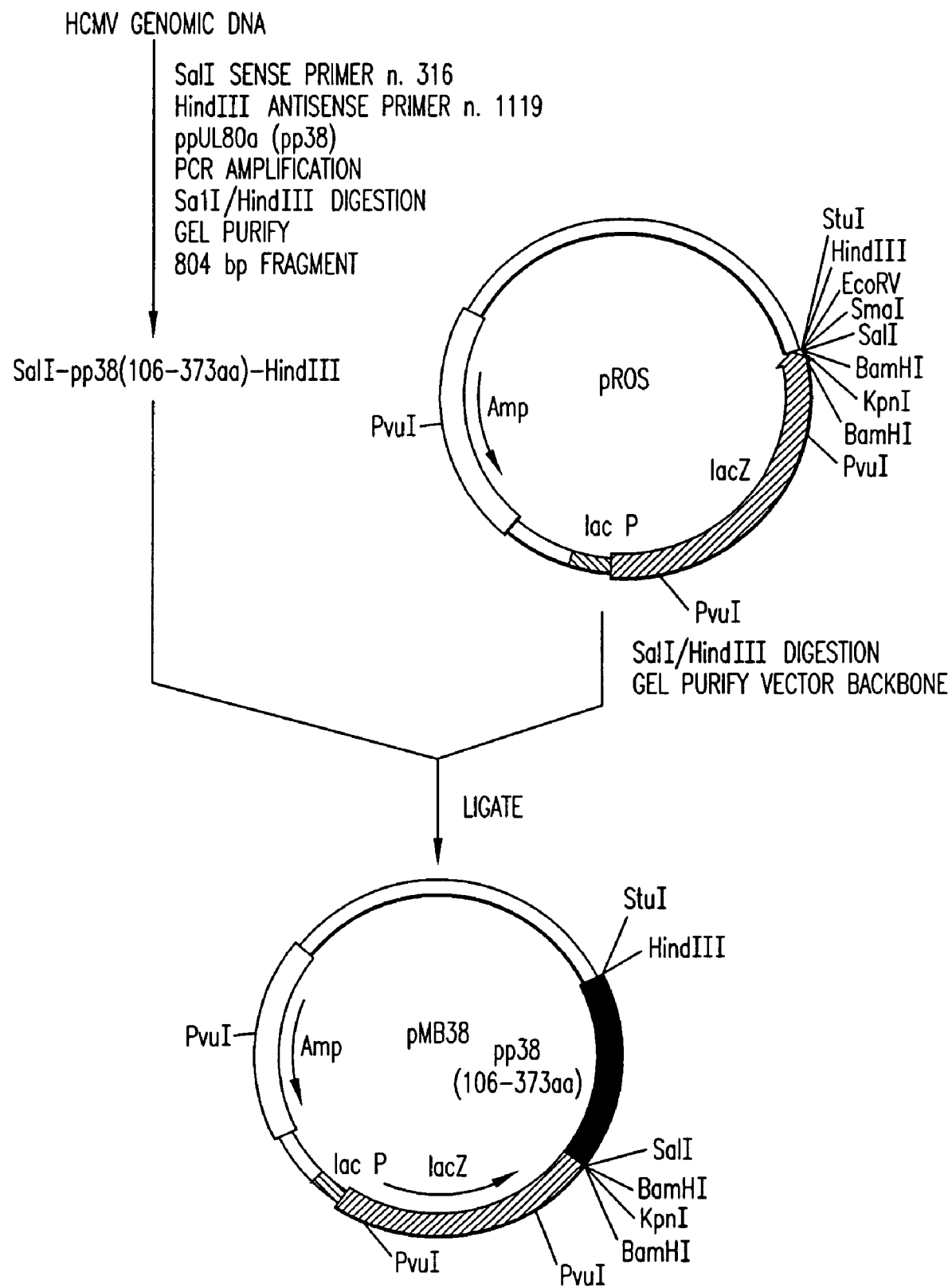
FIG. 6 is a schematic representation of the construction of plasmid pMB38:lacZ-pp38(106-373aa)

The plasmid pMB38, a derivative of the lacZ expression vector pROS (FIG. 6), was constructed by cloning a DNA fragment containing HCMV-pp38(106-373aa) into the polylinker region pROS. The DNA fragment containing HCMV-pp38(106-373aa) was obtained by PCR amplification of genomic HCMV DNA from the region of the ppUL80a gene encoding amino acids 106-373 of the phosphoprotein pp38 (nucleotides 316-1119 of ppUL80a, where nucleotides 1 and 1119 correspond to nucleotides 116203 and 117321, respectively, of the AD169 DNA sequence).

Plasmid pROS was digested with SalI and HindIII, and the resulting vector backbone was purified on an agarose gel. A sense primer, starting at nucleotide 316 of ppUL80a and containing a SalI site, and an antisense primer, starting at nucleotide 1119 of ppUL80a and containing a HindIII site, were synthesized and both primers were added to a PCR reaction mixture containing genomic HCMV DNA. After PCR amplification, the reaction mixture was digested with SalI and HindIII, and the 804 base pair fragment containing pp38(106-373aa) was purified on an agarose gel. This purified fragment then was ligated to purified pROS/SalI/HindIII overnight at 16° C. The ligation mixture was transformed the next day into competent DH5α cells. Miniprep DNA was prepared from the transformants and the transformants were screened for the presence of the 804 base pair pp38(106-373aa) fragment in pROS at the end of the lacZ gene. Plasmid pMB38 contained the pp38(106-373aa) fragment. The DNA sequence of pp38(106-373aa) in pMB38 was confirmed by DNA sequencing, and the pp38(106-373aa) coding region was in-frame with the lacZ coding sequence.

Example 5

Construction of CKS-CMV Expression Vectors Based on pJO200

The CKS expression vector pJO200 was utilized as the starting point for a series of six CKS-CMV gene fusion constructs. Two types of CKS-CMV gene fusion plasmids were constructed. The first, herein referred to as epitope-embedding, was constructed such that the CMV gene DNA sequence was inserted within the CKS gene at nucleotide 638 of pJO200 (corresponding to amino acid 171 of CKS). This construct was designated "CKS(1-171aa)-CMV-CKS(171-260aa)". Fusion proteins expressed in E. coli from this type of construct contain the epitopes of the antigen embedded entirely within the CKS amino acid sequence. Plasmid pCMV-1A (described below) was constructed in this manner.

The second type of CKS-CMV gene fusion plasmid was constructed with the CMV gene DNA sequence linked to the 3' end of the CKS gene at the position corresponding to CKS amino acid 248. This construct was designated "CKS(1-248aa)-CMV". Plasmids pCMV-3A, pCMV-3B, pCMV-4, pCMV-9, and pCMV-26 (described below) were constructed in this manner. Large scale plasmid DNA (pJO200) was isolated by general methods, and was used for the constructs described below.

Step A: Construction of pCMV-1A: CKS-A1C2F3-CKS

Figure 7:
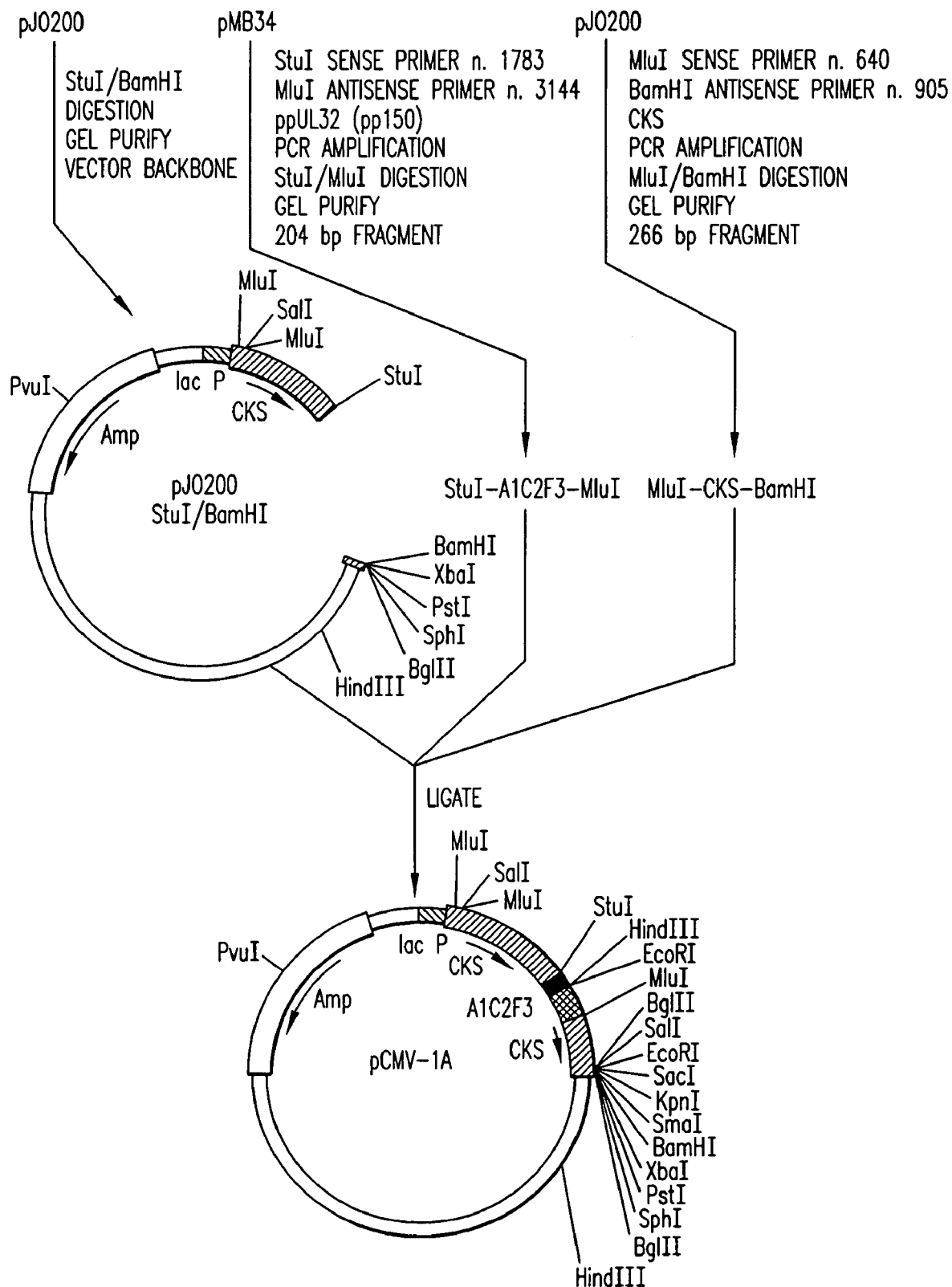
FIG. 7 is a schematic representation of the construction of plasmid pCMV-1A:CKS-A1C2F3-CKS.

The plasmid pCMV-1A, a derivative of plasmid pJO200 (FIG. 7), was constructed by cloning a DNA fragment containing HCMV-A1C2F3, obtained by PCR amplification of A1C2F3 DNA contained in plasmid pMB34, into the StuI site of pJO200.

Large scale plasmid DNA (pMB34) was isolated by general methods. Plasmid pJO200 DNA was digested with StuI and BamHI, and the vector backbone was purified on an agarose gel. The StuI/BamHI digest removed a portion of the 3' end of the CKS gene, which was restored later in the ligation reaction. Two PCR-derived DNA fragments were cloned into this vector backbone in a 3-way ligation reaction. A1C2F3 was cloned as a StuI/MluI DNA fragment and the remaining 3' portion of the CKS gene was cloned as a MluI/BamHI DNA fragment, restoring the complete CKS gene.

A sense primer, starting at nucleotide 1783 of ppUL32 containing a StuI site, and an antisense primer, starting at nucleotide 3144 of ppUL32 containing an MluI site, were synthesized and added to a PCR reaction mixture containing plasmid pMB34. After PCR amplification, the reaction mixture was digested with StuI and MluI, and the 204 base pair fragment containing A1C2F3 was purified on an agarose gel. A sense primer starting at nucleotide 640 of pJO200 (containing an MluI site), and an antisense primer starting at nucleotide 905 of pJO200, were synthesized and added to a PCR reaction mixture containing plasmid pJO200. (The above nucleotide numberings correspond to the DNA sequence shown in FIG. 12.) After PCR amplification, the reaction mixture was digested with MluI and BamHI, and the 266 base pair fragment containing the 3' portion of the CKS gene was gel purified. These purified PCR-derived DNA fragments were then ligated to pJO200/StuI/BamHI overnight at 16° C. The next day the ligation mixture was transformed into competent XL-1 Blue cells.

Miniprep DNA was prepared from the transformants and screened for the presence of A1C2F3 inserted at the StuI site of pJO200. Plasmid pCMV-1A contained A1C2F3 inserted at the StuI site. The DNA sequence of A1C2F3 and the 3' end of the CKS gene was confirmed by DNA sequencing. The coding region of the CKS-A1C2F3-CKS construct which encodes the protein rpCMV-1A contained a bridge of two amino acids (threonine and arginine) contributed from the MluI site between A1C2F3 and the 3' end of CKS. In addition, amino acid 171 of CKS was duplicated in the construct, which was designated "CKS(1-171aa)-A1C2F3-T-R-CKS (171-260aa)".

Step B: Construction of pCMV-3A: CKS-A1C2F3

Figure 8A:
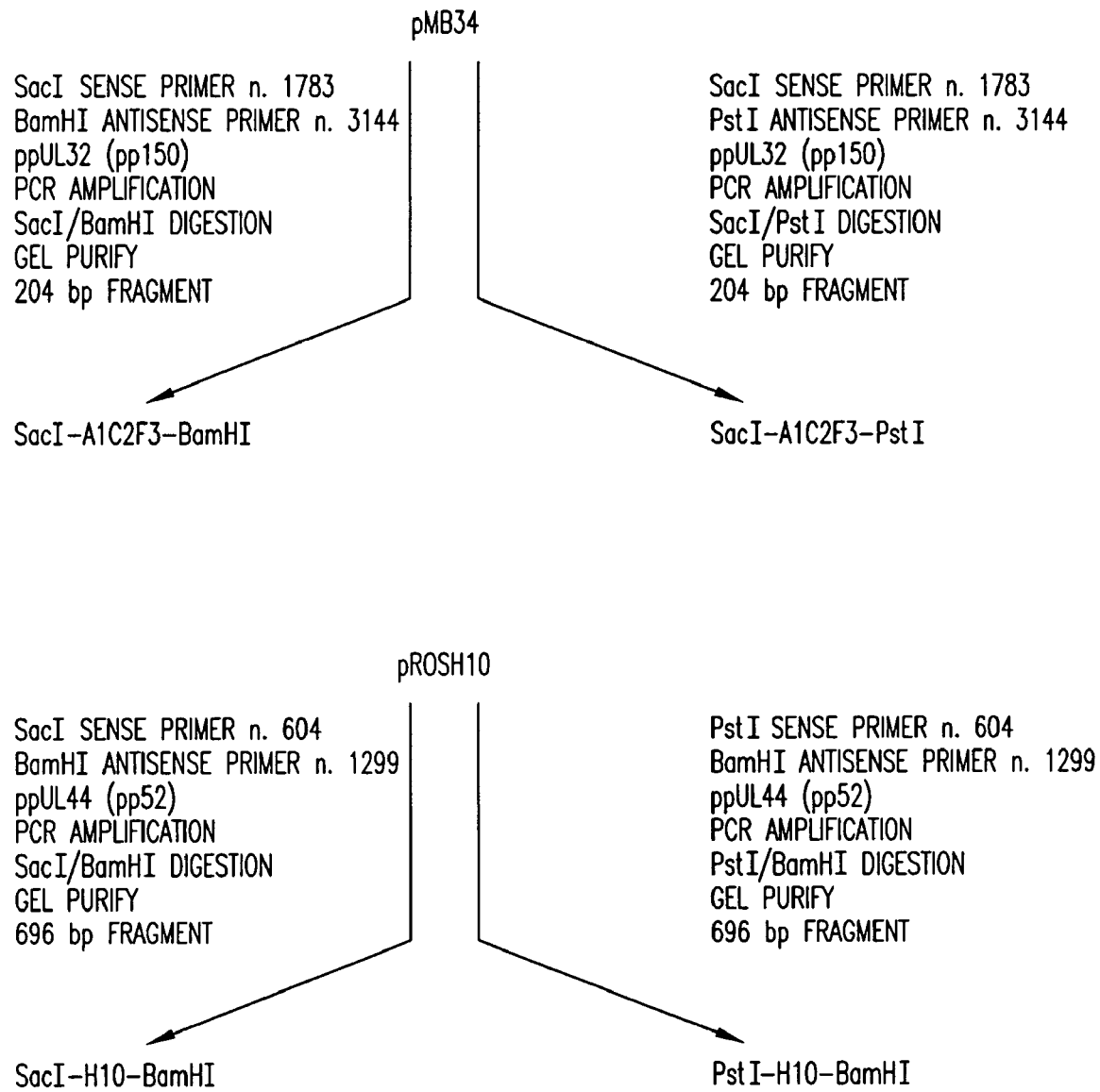
FIG. 8 is a schematic representation of (A) the preparation of PCR fragments containing the A1C2F3 and H10 DNA sequences; (B) the preparation of PCR fragments containing the pp65(297-510aa) and pp38(117-373aa) DNA sequences, and (C) the construction of plasmid pCMV-3A; CKS-A1C2F3, plasmid pCMV-3B:CKS-H10, plasmid pCMV-4: CKS-A1C2F3-H10, plasmid pCMV-9: CKS-pp65(297-510aa) and plasmid pCMV-26:CKS-pp38(117-373aa)
Figure 8B:
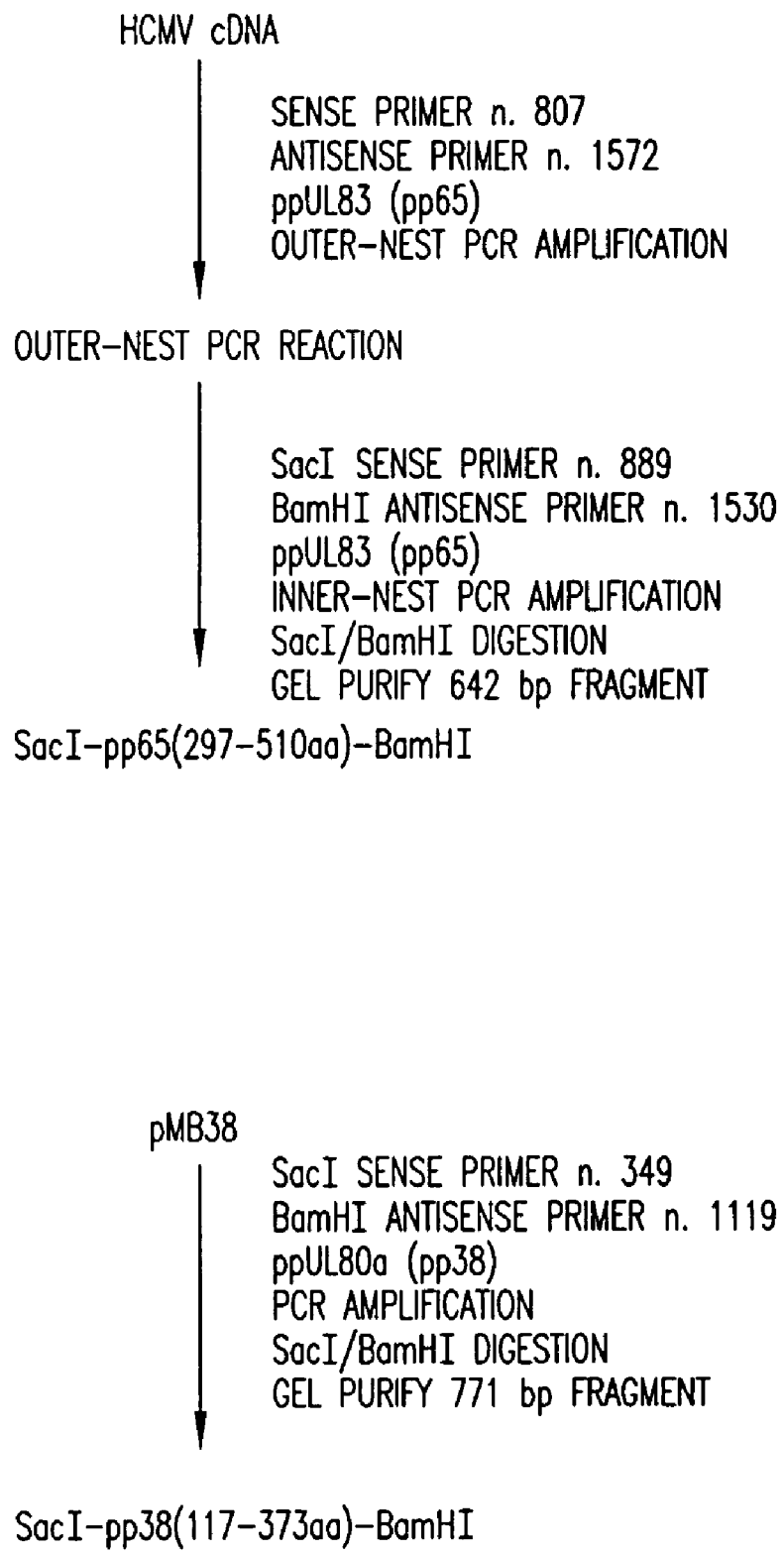
Figure 8C:
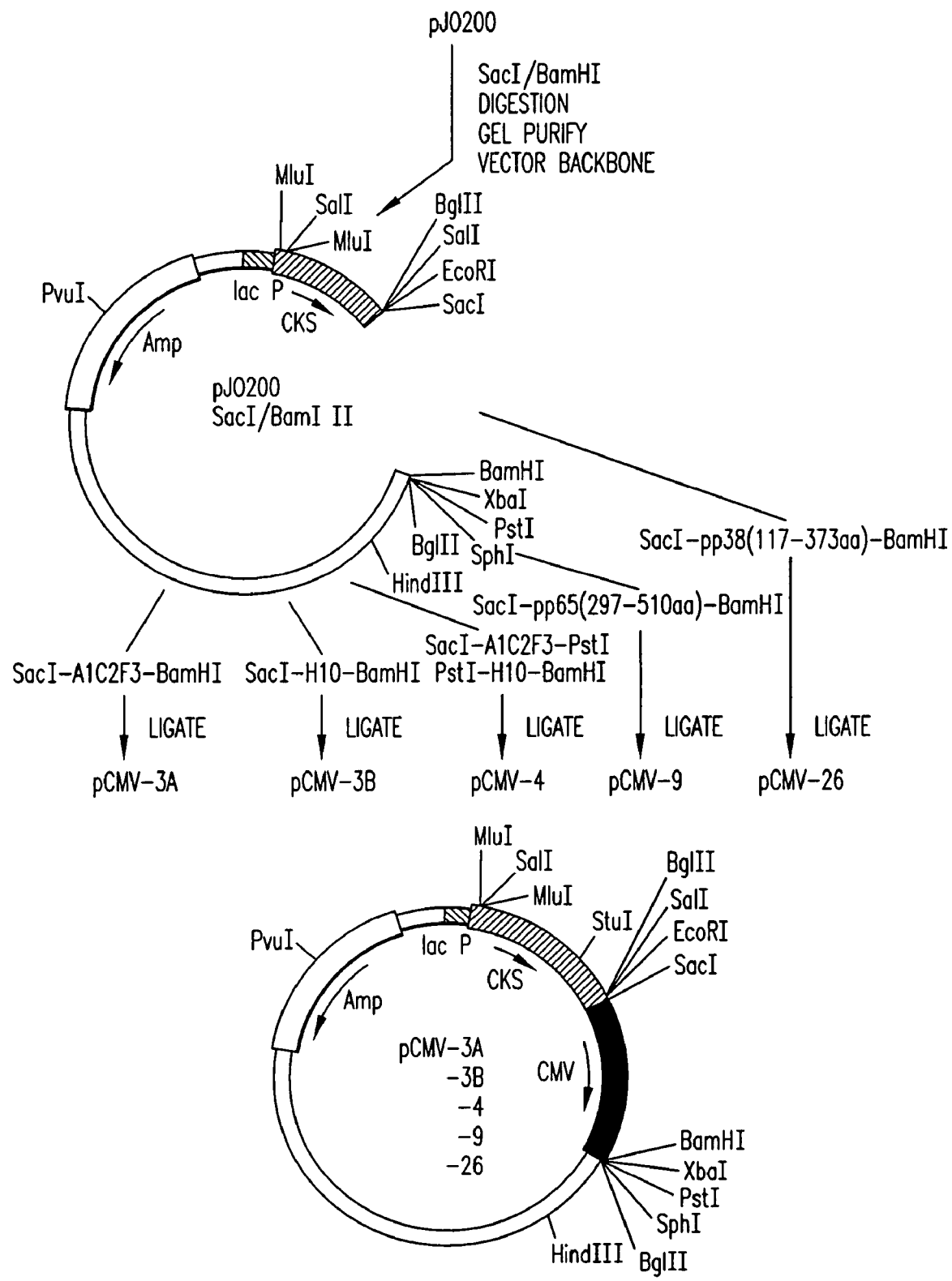

The plasmid pCMV-3A, a derivative of plasmid pJO200 (FIGS. 8A and C), was constructed by cloning a DNA fragment containing HCMV-A1C2F3, obtained by PCR amplification of A1C2F3 DNA contained in plasmid pMB34, into the SacI/BamHI sites of pJO200. Plasmid pJO200 was digested with SacI and BamHI, and the vector backbone was purified on an agarose gel. A sense primer, starting at nucleotide 1783 of ppUL32 containing a SacI site, and an antisense primer, starting at nucleotide 3144 of ppUL32 containing a stop codon at the end of the A1C2F3 coding sequence followed by a BamHI site, were synthesized and added to a PCR reaction mixture containing plasmid pMB34. After PCR amplification, the reaction mixture was digested with SacI and BamHI, and the 204 base pair fragment containing A1C2F3 was purified on an agarose gel and then ligated to pJO200/SacI/BamHI overnight at 16° C.

The ligation mixture was transformed the next day into competent XL-1 Blue cells. Miniprep DNA was prepared from the transformants and screened for the presence of the 204 base pair fragment in pJO200 at the SacI/BamHI sites. Plasmid pCMV-3A contained the A1C2F3 fragment fused in-frame with the CKS gene. The DNA sequence of A1C2F3 and the 3' end of the CKS gene was confirmed. This CKS-CMV fusion construct was designated "CKS(1-248aa)-A1C2F3".

Step C: Construction of pCMV-3B: CKS-H10

The plasmid pCMV-3B, another derivative of plasmid pJO200, was constructed by cloning a DNA fragment containing HCMV-H10 from plasmid pROSH10, described in Ripalti et al., J. Virological Methods 46:39 (1994), into pJO200. The H10 DNA sequence was derived from ppUL44, which encodes a phosphoprotein of 52 kD from HCMV. The H10 portion of ppUL44 in pROSH10 contained nucleotides 604-1299 of ppUL44, where nucleotides 1 and 1299 correspond to nucleotides 56512 and 55214, respectively, of the complementary strand of the AD169 DNA sequence). H10 encodes the C-terminal half of phosphoprotein pp52, corresponding to amino acids 202-434. Plasmid pCMV-3B was constructed by cloning the H10 DNA fragment from pROSH10, obtained by PCR amplification of the H10 DNA sequence, into the SacI/BamHI sites of pJO200.

Plasmid pJO200 was digested with SacI and BamHI and the vector backbone was purified on an agarose gel. A sense primer, starting at nucleotide 604 of ppUL44 containing a SacI site, and an antisense primer, starting at nucleotide 1299 of ppUL44 containing a stop codon at the end of the H10 coding sequence followed by a BamHI site, were synthesized and added to a PCR reaction mixture containing plasmid pROSH10. After PCR amplification, the reaction mixture was digested with SacI and BamHI, and the 696 base pair fragment containing H10 was purified on an agarose gel and then ligated to pJO200/SacI/BamHI overnight at 16° C. The ligation mixture was transformed the next day into competent XL-1 Blue cells. Miniprep DNA was prepared from the transformants and screened for the presence of the 696 base pair fragment in pJO200 at the SacI/BamHI sites. Plasmid pCMV-3B contained the H10 fragment fused in-frame with the CKS gene. The DNA sequence of H10 and the 3' end of the CKS gene was confirmed. This CKS-CMV fusion construct was designated "CKS(1-248aa)-H10".

Step D: Construction of pCMV-4: CKS-A1C2F3-H10

The plasmid pCMV-4, a further derivative of pJO200, was constructed by cloning PCR amplified DNA fragments, containing both HCMV-A1C2F3 and HCMV-H10 derived from pMB34 and pROSH10, respectively, into pJO200.

Plasmid pJO200 was digested with SacI and BamHI and the vector backbone was purified on an agarose gel. Two PCR-derived DNA fragments were cloned in a 3-way ligation reaction into this vector backbone. A1C2F3 was cloned as a SacI/PstI DNA fragment and H10 was cloned as a PstI/BamHI DNA fragment.

A sense primer, starting at nucleotide 1783 of ppUL32 containing a SacI site, and an antisense primer, starting at nucleotide 3144 of ppUL32 containing an PstI site, were synthesized and added to a PCR reaction mixture containing plasmid pMB34. After PCR amplification, the reaction mixture was digested with SacI and PstI, and the 204 base pair fragment containing A1C2F3 was purified on an agarose gel. A sense primer, starting at nucleotide 604 of ppUL44 containing a PstI site, and an antisense primer, starting at nucleotide 1299 of ppUL44 containing a stop codon at the end of the H10 coding sequence followed by a BamHI site, were synthesized and added to a PCR reaction mixture containing plasmid pROSH10. After PCR amplification, the reaction mixture was digested with PstI and BamHI, and the 696 base pair fragment containing H10 was purified on an agarose gel.

The HCMV-A1C2F3 and HCMV-H10 purified PCR-derived DNA fragments were then ligated to pJO200/SacI/BamHI overnight at 16° C. The ligation mixture was transformed the next day into competent XL-1 Blue cells. Miniprep DNA was prepared from the transformants and screened for the presence of A1C2F3 and H10 inserted at the SacI/BamHI sites of pJO200. Plasmid pCMV-4 contained A1C2F3 and H10 at the end of the CKS gene in pJO200. The DNA sequence of A1C2F3 and H10 was confirmed. The coding region of the CKS-A1C2F3-H10 construct which encodes for the recombinant protein rpCMV-4 contained a bridge of two amino acids contributed from the PstI site between A1C2F3 and H10. This CKS-CMV fusion construct was designated "CKS(1-248aa)-A1C2F3-L-Q-H10". The entire construct, including the dipeptide insert, is herein referred to as "A1C2F3-H10".

Step E: Construction of pCMV-9: CKS-pp65(297-510aa)

The plasmid pCMV-9, yet another derivative of pJO200, was constructed by cloning a DNA fragment containing HCMV-pp65(297-510aa), obtained by PCR amplification of HCMV cDNA from the region of ppUL83 encoding amino acids 297-510 of pp65, into pJO200. The fragment used consisted of nucleotides 889-1530 of ppUL83, where nucleotides 1 and 1683 correspond to nucleotides 121037 and 119355, respectively, of the complementary strand of the AD169 DNA sequence.

A two-stage nested PCR reaction was used to generate the HCMV-pp65(297-510aa) DNA fragment using HCMV cDNA as template. For the outer nest PCR amplification reaction, a sense primer, starting at nucleotide 807 of ppUL83, and an antisense primer, starting at nucleotide 1572 of ppUL83, were synthesized and added to a PCR reaction mixture containing HCMV cDNA. After PCR amplification, the outer nest PCR reaction mixture was used as template DNA for the inner nest PCR amplification reaction. For the inner nest PCR amplification reaction, a sense primer, starting at nucleotide 889 of ppUL83 containing a SacI site, and an antisense primer, starting at nucleotide 1530 of ppUL83 containing a stop codon at the end of the pp65(297-510aa) coding sequence followed by a BamHI site, were synthesized and added to a PCR reaction mixture containing outer nest amplified DNA. After PCR amplification, the reaction mixture was digested with SacI and BamHI, and the 642 base pair fragment containing pp65(297-510aa) was purified on an agarose gel.

Plasmid pJO200 was digested with SacI and BamHI and the vector backbone was purified on an agarose gel. The HCMV-pp65(297-510aa) purified DNA fragment then was ligated to pJO200/SacI/BamHI overnight at 16° C. The ligation mixture was transformed the next day into competent XL-1 Blue cells. Miniprep DNA was prepared from the transformants and screened for the presence of pp65(297-510aa) inserted at the SacI/BamHI sites of pJO200. Plasmid pCMV-9 contained pp65(297-510aa) at the end of the CKS gene in pJO200. The DNA sequence of pp65(297-510aa) was confirmed. This CKS-CMV fusion construct was designated "CKS(1-248aa)-pp65(297-510aa)".

Step F: Construction of pCMV-26: CKS-pp38(117-373aa)

The plasmid pCMV-26, still another derivative of pJO200, was constructed by cloning a DNA fragment containing HCMV-pp38(117-373aa), obtained by PCR amplification of pp38 DNA from the region of ppUL80a encoding amino acids 117-373 of pp38 (nucleotides 349-1119) derived from pMB38, into pJO200.

A sense primer, starting at nucleotide 349 of ppUL80a containing a SacI site, and an antisense primer, starting at nucleotide 1119 of ppUL80a containing a stop codon followed by a BamHI site, were synthesized and added to a PCR reaction mixture containing pMB38 DNA. After PCR amplification, the reaction mixture was digested with SacI and BamHI, and the 771 base pair fragment containing pp38(117-373aa) was purified on an agarose gel.

Large scale plasmid DNA (pMB34) was isolated by general methods. Plasmid pJO200 was digested with SacI and BamHI and the vector backbone was purified on an agarose gel. The HCMV-pp38(117-373aa) purified DNA fragment then was ligated to pJO200/SacI/BamHI overnight at 16° C. The ligation mixture was transformed the next day into competent XL-1 Blue cells. Miniprep DNA was prepared from the transformants and screened for the presence of pp38(117-373aa) inserted at the SacI/BamHI sites of pJO200. Plasmid pCMV-26 contained pp38(117-373aa) at the end of the CKS gene in pJO200. The DNA sequence of pp38(117-373aa) was confirmed. This CKS-CMV fusion construct was designated "CKS(1-248aa)-pp38(117-373aa)".

Example 6

Construction of CKS Epitope-Embedding Expression Vector pEE1

A CKS epitope-embedding expression vector was prepared which allowed for the embedding of epitope-containing recombinant proteins within the CKS protein. The vector, herein referred to as pEE1, was also designated "CKS(1-171aa)-Recombinant Protein-T-R-CKS(171aa-260)". This pEE1 vector was constructed in two steps starting with the CKS expression vector pJO200. In the first step, a mutagenic oligonucleotide was cloned into a pair of adjacent MluI sites located near the 5' end of the CKS gene in pJO200, removing both MluI sites and a SalI site. This modification to pJO200 allows the use of a unique MluI cloning site to be introduced further downstream in the CKS gene in the next step. In the second step, a fragment of DNA from plasmid pCMV-1A was cloned into this modified pJO200 vector, thus permitting the embedding of genes as StuI/MluI fragments into the CKS gene.

Step A: Construction of pJO200-ΔMluI

Figure 9A:
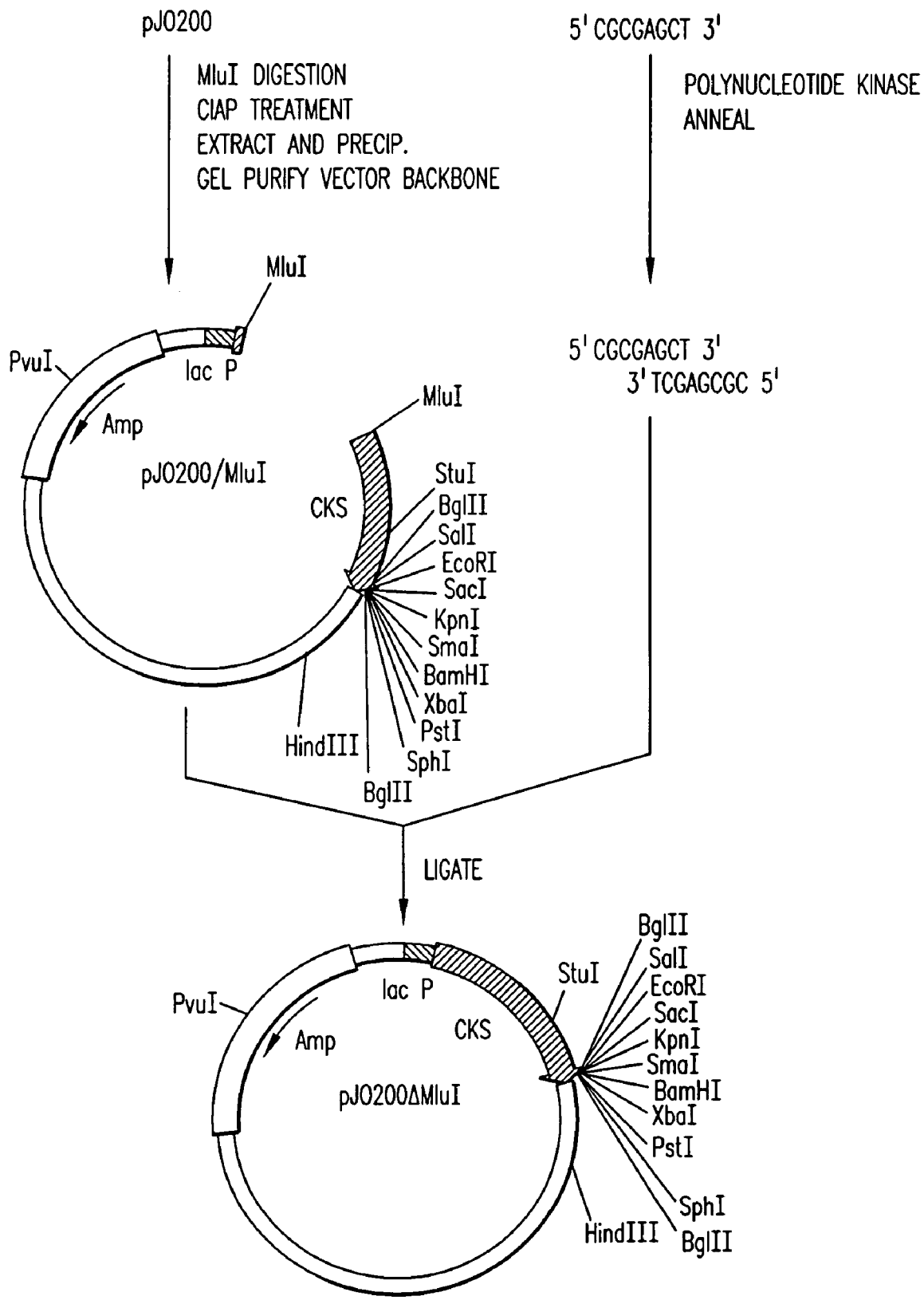
FIG. 9 is a schematic representation of (A) the construction of plasmid pJO200-ΔM1ul; (B) the nucleotide sequence of the plasmid pJO200, including the intended modification site at plasmid residues 151 to 180 (5'-3') (SEQ ID NO:4); (C) the double-stranded structure of the mutagenic oligonucleotide, 5'CGCGACGT3', synthesized for ligation into plasmid pJO200/M1ul/CIAP; and (D) the nucleotide sequence of the plasmid pJO200 ΔM1ul, including the modified residues 151 to 180 (5'-3') (SEQ ID NO:6)

The plasmid pJO200ΔMluI, a derivative of the CKS expression vector pJO200 (FIG. 9A), was constructed by removing a pair of adjacent MluI sites and a SalI site located at nucleotides 161-174 (amino acids 11-15) in the pJO200 DNA sequence using a mutagenic oligonucleotide. The modification site of the native pJO200 DNA sequence was contained in the nucleotide sequence 151-180 5'-3' [SEQ ID NO:4] (FIG. 9B). The two targeted mutagenic nucleotides, pJO200 DNA thymine-166 and pJO200 DNA adenine-169, as well as the two MluI sites and the SalI site, are noted.

Plasmid pJO200 was digested with MluI, precipitated with ethanol and resuspended in alkaline phosphatase buffer. Plasmid pJ200/MluI then was treated with calf intestinal alkaline phosphatase (CIAP) to remove the 5' phosphate groups to prevent self-ligation. The DNA was extracted with phenol-chloroform after treatment with CIAP, was precipitated with ethanol, and was resuspended in TE buffer. The vector backbone was then purified on an agarose gel.

The mutagenic oligonucleotide of FIG. 9C was synthesized for ligation into pJO200/MluI/CIAP. This oligonucleotide was self-complementary at its 3' end and was capable of forming a double-stranded structure after a heat denaturation step followed by an annealing step. The mutagenic oligonucleotide contained MluI sticky-ends permitting ligation into MluI digested pJO200 DNA. The sequence of this oligonucleotide differed from the native pJO200 DNA sequence in that the pJO200 DNA T166 and pJO200 DNA A169 residues were reversed in the mutagenic oligonucleotide (FIGS. 9C and D, as noted by the underline). Thus, when the mutagenic oligonucleotide was cloned into the MluI site of pJO200, it destroyed both MluI sites and the SalI site.

The synthetic mutagenic oligonucleotide was phosphorylated at its 5' end using polynucleotide kinase. The reaction mixture was heated to 65° C. for 20 minutes to inactivate the kinase. After cooling to room temperature, the phosphorylated oligonucleotide was mixed with the pJO200/MluI/CIAP, heated at 65° C. for 5 minutes, and then cooled to room temperature gradually to permit annealing of the phosphorylated oligonucleotide to itself. Ligation buffer and T4 DNA ligase were then added, and the mixture was incubated overnight as the temperature was lowered from 20° C. to 4° C. The ligation mixture was transformed the next day into competent XL-1 Blue cells. Miniprep DNA was prepared from the transformants and screened for the loss of the MluI and SalI sites. Plasmid pJO200ΔMluI was isolated which has lost these restriction enzyme sites. The DNA sequence of the 5' end of the CKS gene was confirmed by DNA sequencing. In addition to removing the MluI and SalI sites, the mutagenic oligonucleotide changed the amino acids coded by nucleotides 166-171 from Ser-Thr to Thr-Ser. The plasmid pJO200 DNA sequence was thereby modified to the plasmid pJO200ΔMluI DNA, having the partial sequence of nucleotides 151-180 5'-3' [SEQ ID NO:6] of FIG. 9D.

Step B: Construction of pEE1

Figure 10:
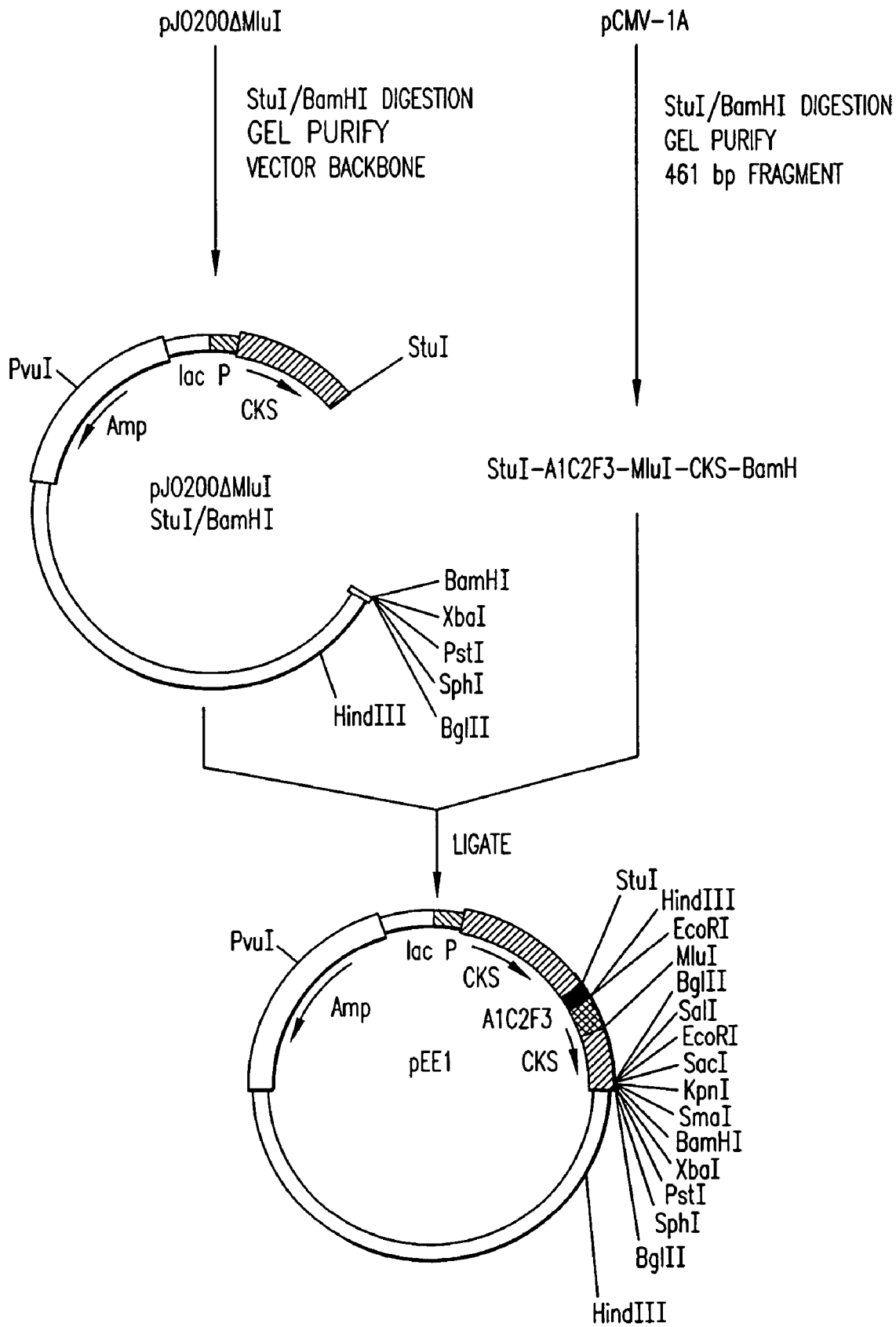
FIG. 10 is a schematic representation of the construction of plasmid pEE1.

The plasmid pEE1, a derivative of the plasmid pJO200ΔMluI (FIG. 10), was constructed by cloning a StuI/BamHI fragment from plasmid pCMV-1A, which contained HCMV-A1C2F3 embedded within the CKS gene, into the StuI/BamHI sites of pJO200ΔMluI. By substituting the StuI/BamHI DNA fragment within the CKS coding region present in pJO200ΔMluI with the StuI/BamHI fragment from plasmid pCMV-1A, the resulting plasmid pEE1 contained HCMV-A1C2F3 embedded within the CKS gene. Plasmid pEE1 differed from plasmid pCMV-1A in that pEE1 did not contain the upstream MluI sites present in the 5' end of the CKS gene. Hence, digestion of pEE1 with StuI and MluI would release the HCMV-A1C2F3 DNA fragment and provide a vector backbone after purification on an agarose gel capable of accepting other genes for embedding into the CKS gene as blunt/MluI compatible sticky-end DNA fragments.

Large scale plasmid DNAs (pJO200ΔMluI and pCMV-1A) were isolated by general methods. Plasmid pCMV-1A was digested with StuI and BamHI and the 461 base pair fragment, containing A1C2F3 and the 3' end of the CKS gene, was purified on an agarose gel. Plasmid pJO200ΔMluI was digested with StuI and BamHI and the vector backbone was purified on an agarose gel. The 461 base pair fragment containing A1C2F3 and the pJO200ΔMluI/StuI/BamHI vector backbone were mixed together and ligated overnight at 16° C. The ligation mixture was transformed the next day into competent XL-1 Blue cells. Miniprep DNA was prepared from the transformants and screened for the presence of the 461 base pair A1C2F3 DNA fragment in pJO200ΔMluI. Plasmid pEE1 contained the A1C2F3 DNA fragment and no MluI sites in the 5' end of the CKS gene. The DNA sequence of the 3' end of the CKS gene and the A1C2F3 fragment was confirmed by DNA sequencing. Digestion of plasmid pEE1 with StuI and BamHI, followed by purification of the vector backbone on an agarose gel, removed the A1C2F3 DNA fragment completely in preparation for ligation with other DNA fragments. This purified vector backbone could accept DNA fragments for embedding into the CKS gene in the correct reading frame, schematically represented as "5'X-Gene of Interest-Y 3'" where X is a blunt end and Y is an MluI-compatible sticky end, as for example MluI or BssHII. Plasmid pEE1 was deposited with the American Type Culture Collection (ATCC), 12301 Parklawn Drive, Rockville, Md. 20852 (USA) under terms of the Budapest Treaty on May 1, 1995, and was accorded Accession No. ATCC 69798.

Example 7

Construction of CKS Epitope-Embedding Expression Vectors Based on pEE1

The CKS expression vector pEE1 was utilized as the starting point for a series of four CKS-CMV-CKS gene fusion constructs. For each construct, plasmid pEE1 was digested with StuI and MluI and the vector backbone was purified. The pEE1/StuI/MluI backbone was able to accept CMV gene fragments generated by PCR which had a StuI site at their 5' end and a MluI site at their 3' end. After digestion with StuI and MluI, the PCR fragments were cloned in-frame into the pEE1/StuI/MluI backbone. The CKS-CMV-CKS fusion proteins expressed from these vectors were designated "CKS(1-171aa)-CMV-T-R-CKS(171-260aa)", where T and R are threonine and arginine residues encoded by the synthetic MluI site introduced into the vector.

Step A: Construction of pCMV-27: CKS-A1C2F3-H10-CKS

Figure 11A:
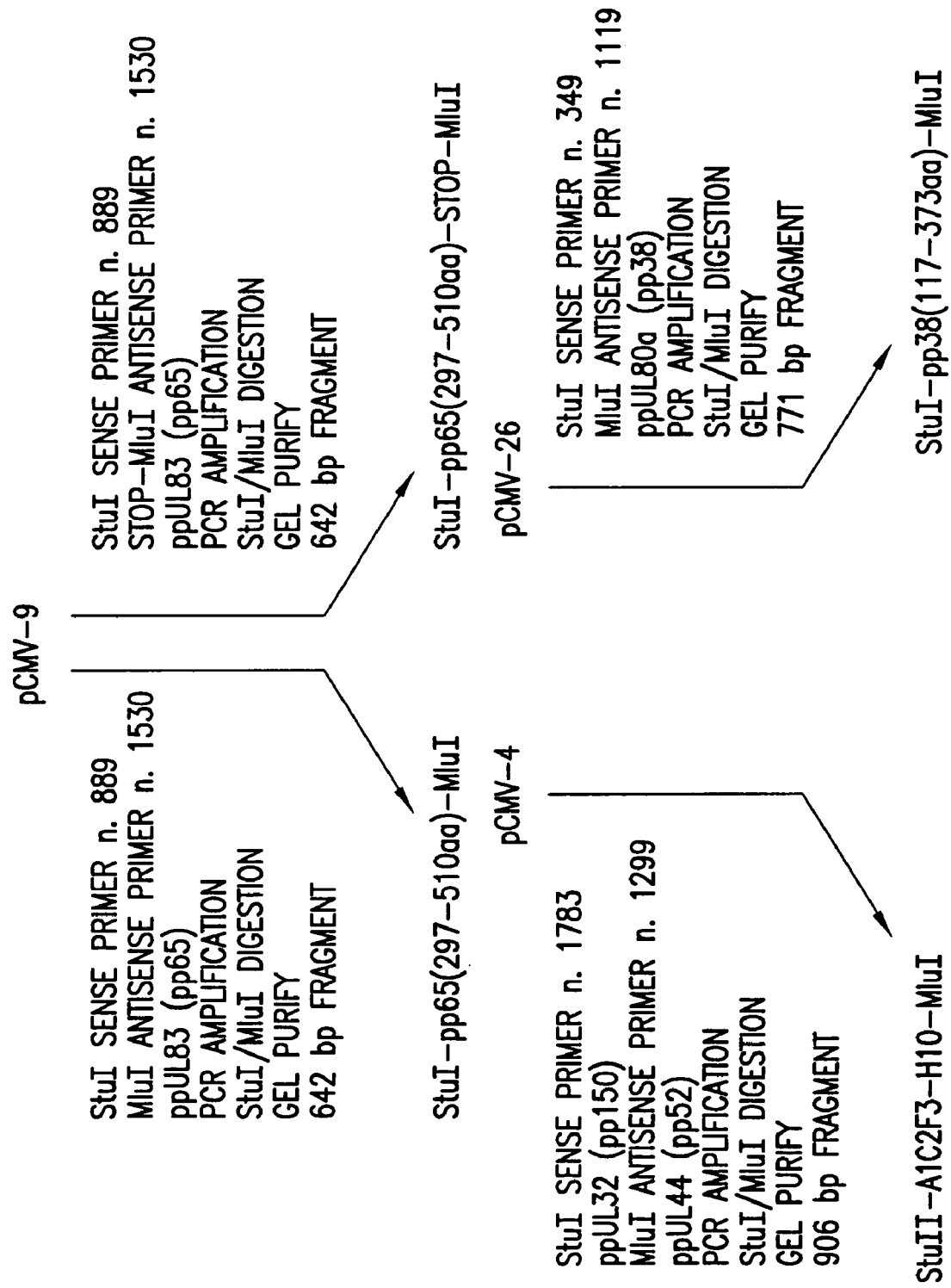
FIG. 11 is a schematic representation of (A) the preparation of PCR fragments containing the A1C2F3-H10, pp65(297-510aa), and pp38(117-373aa) DNA sequences; and (B) the construction of plasmid pCMV-27: CKS-A1C2F3-H10-CKS, plasmid pCMV-28:CKS-pp65(297-510aa)-CKS, plasmid pCMV-28STOP:CKS-pp65(297-510aa)-STOP-CKS, and plasmid pCMV-29:CKS-pp38(117-373aa)-CKS.
Figure 11B:
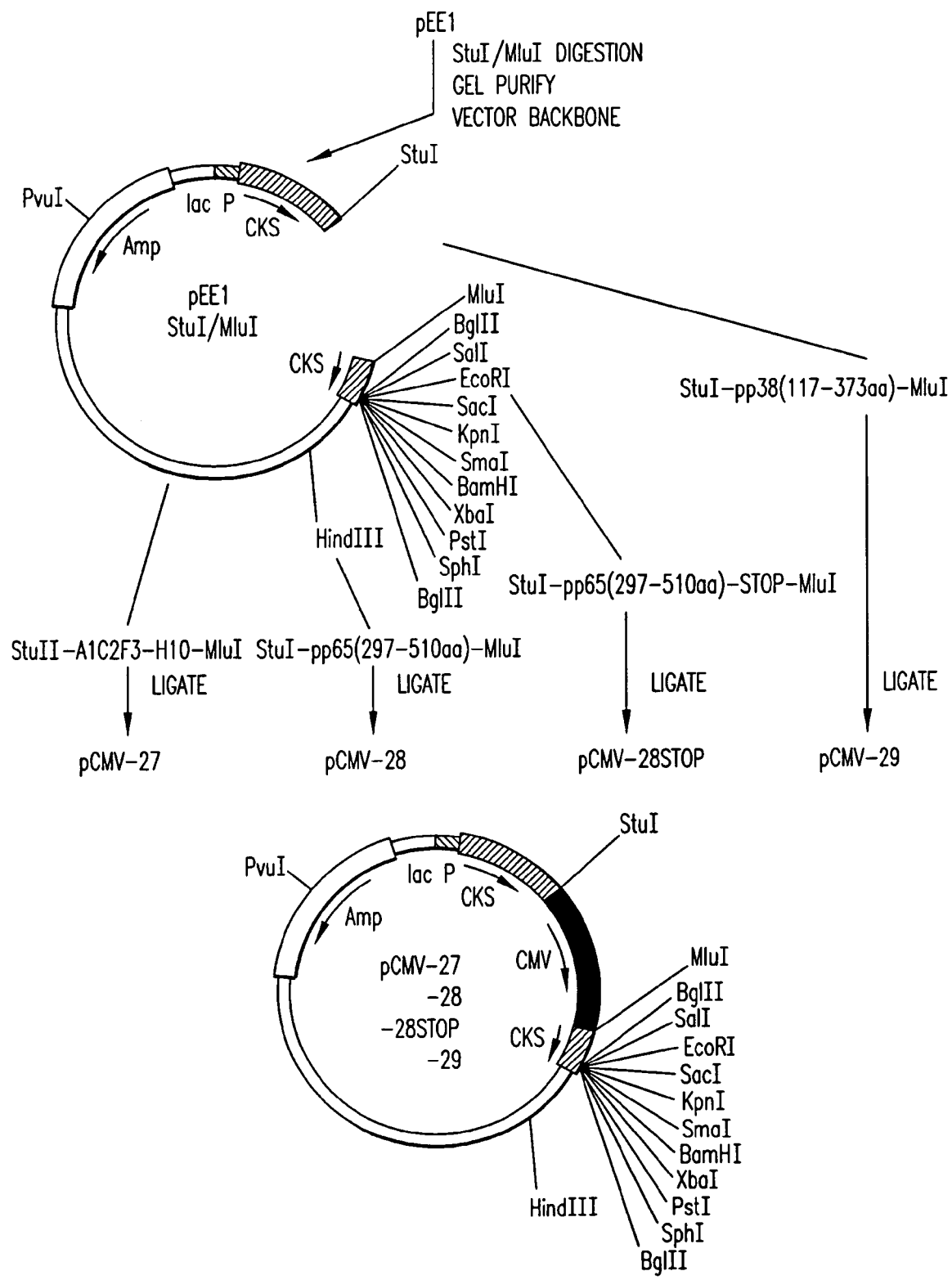

The plasmid pCMV-27, a derivative of pEE1 (FIGS. 11A and B), was constructed by cloning a PCR amplified DNA fragment, containing HCMV-A1C2F3-H10 derived from pCMV-4, into pEE1. Plasmid pCMV-27 was deposited with the American Type Culture Collection (ATCC), 12301 Parklawn Drive, Rockville, Md. 20852 (USA) under terms of the Budapest Treaty on May 1, 1995, and was accorded Accession No. ATCC 69797.

Large scale plasmid DNAs (pEE1 and pCMV-4) were isolated by general methods. Plasmid pEE1 was digested with StuI and MluI and the vector backbone, pEE1/StuI/MluI, was purified on an agarose gel. A sense primer, starting at nucleotide 1783 of ppUL32 containing a StuI site, and an antisense primer, starting at nucleotide 1299 of ppUL44 containing an MluI site, were synthesized and added to a PCR reaction mixture containing plasmid pCMV-4. After PCR amplification, the reaction mixture was digested with StuI and MluI, and the 906 base pair fragment containing A1C2F3-H10 was purified on an agarose gel. The purified 906 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the A1C2F3-H10 DNA fragment inserted at the StuI/MluI sites of pEE1. Plasmid pCMV-27 contained A1C2F3-H10 embedded at the StuI/MluI sites of pEE1. The DNA sequence of A1C2F3-H10 and the adjacent DNA sequence of CKS was confirmed by DNA sequencing. This CKS-CMV-CKS fusion construct was designated "CKS(1-171aa)-A1C2F3-L-Q-H10-T-R-CKS (171-260)" where L and Q, and T and R, are the leucine, glutamine, threonine and arginine residues encoded by the synthetic PstI and MluI sites, respectively, introduced into the vector.

Step B: Construction of pCMV-28: CKS-pp65(297-510aa)-CKS

The plasmid pCMV-28, another derivative of pEE1, was constructed by cloning a PCR amplified DNA fragment, containing HCMV-pp65(297-510aa) derived from pCMV-9, into pEE1. Plasmid pCMV-28 was deposited with American Type Culture Collection (ATCC), 12301 Parklawn Drive, Rockville, Md. 20852 (USA) under terms of the Budapest Treaty on May 1, 1995, and was accorded Accession No. ATCC 69799.

Large scale plasmid DNAs (pEE1 and pCMV-9) were isolated by general methods. Plasmid pEE1 was digested with StuI and MluI and the vector backbone was purified on an agarose gel. A sense primer, starting at nucleotide 889 of ppUL83 containing a StuI site, and an antisense primer, starting at nucleotide 1530 of ppUL83 containing an MluI site, were synthesized and added to a PCR reaction mixture containing plasmid pCMV-9. After PCR amplification, the reaction mixture was digested with StuI and MluI, and the 642 base pair fragment containing pp65(297-510aa) was purified on an agarose gel. The purified 642 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the pp65(297-510aa) DNA fragment inserted at the StuI/MluI sites of pEE1. Plasmid pCMV-28 contained pp65(297-510aa) embedded at the StuI/MluI sites of pEE1. The DNA sequence of pp65(297-510aa) and the adjacent DNA sequence of CKS was confirmed by DNA sequencing. This CKS-CMV-CKS fusion construct was designated "CKS (1-171aa)-pp65(297-510aa)-T-R-CKS(171-260)" where T and R are the threonine and arginine residues encoded by the synthetic MluI sites introduced into the vector.

Step C: Construction of pCMV-28STOP: CKS-pp65(297-510aa)-STOP-CKS

The plasmid pCMV-28STOP, a further derivative of pEE1, was constructed by cloning a PCR amplified DNA fragment, containing HCMV-pp65(297-510aa) derived from pCMV-9, into pEE1. When translated, the plasmid produced a truncated form of the recombinant protein rpCMV-28, as described below.

Large scale plasmid DNAs (pEE1 and pCMV-9) were isolated by general methods. Plasmid pEE1 was digested with StuI and MluI and the vector backbone was purified on an agarose gel. A sense primer, starting at nucleotide 889 of ppUL83 containing a StuI site, and an antisense primer, starting at nucleotide 1530 of ppUL83 containing a stop codon followed by an MluI site, were synthesized and added to a PCR reaction mixture containing plasmid pCMV-9. After PCR amplification, the reaction mixture was digested with StuI and MluI, and the 642 base pair fragment containing pp65(297-510aa) was purified on an agarose gel. The purified 642 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the pp65(297-510aa) DNA fragment inserted at the StuI/MluI sites of pEE1. Plasmid pCMV-28 contained pp65 (297-510aa) embedded at the StuI/MluI sites of pEE1. The DNA sequence of pp65(297-510aa) and the adjacent DNA sequence of CKS was confirmed. This CKS-CMV-CKS fusion construct was designated "CKS(1-171aa)-pp65(297-510aa)-STOP-T-R-CKS(171-260)" where STOP is the stop codon and T and R are the threonine and arginine residues encoded by the synthetic MluI sites introduced into the vector. Due to the presence of the stop codon at the end of the pp65 coding sequence, the remaining coding sequence for the C-terminal region of the CKS protein was not translated and expressed in *E. coli* from this construct.

Step D: Construction of pCMV-29: CKS-pp38(117-373aa)-CKS

The plasmid pCMV-29, a derivative of pEE1, was constructed by cloning a PCR amplified DNA fragment, containing HCMV-pp38(117-373aa) derived from pCMV-26, into pEE1. Plasmid pCMV-29 was deposited with American Type Culture Collection (ATCC), 12301 Parklawn Drive, Rockville, Md. 20852 (USA) under terms of the Budapest Treaty on May 1, 1995, and was accorded Accession No. ATCC 69796.

Large scale plasmid DNAs (pEE1 and pCMV-26) were isolated by general methods. Plasmid pEE1 was digested with StuI and MluI and the vector backbone was purified on an agarose gel. A sense primer, starting at nucleotide 349 of ppUL80a containing a StuI site, and an antisense primer, starting at nucleotide 1119 of ppUL80a containing an MluI site, were synthesized and added to a PCR reaction mixture containing plasmid pCMV-26. After PCR amplification, the reaction mixture was digested with StuI and MluI, and the 771 base pair fragment containing pp38(117-373aa) was purified on an agarose gel. The purified 771 base pair DNA fragment was ligated to pEE1/StuI/MluI overnight at 16° C. The ligation mixture was transformed the next day into competent XL-1 Blue cells. Miniprep DNA was prepared from the transformants and screened for the presence of the pp38(117-373aa) DNA fragment inserted at the StuI/MluI sites of pEE1. Plasmid pCMV-29 contained pp38(117-373aa) embedded at the StuI/MluI sites of pEE1. The DNA sequence of pp38(117-373aa) and the adjacent DNA sequence of CKS was confirmed by DNA sequencing. This CKS-CMV-CKS fusion construct was designated "CKS(1-171aa)-pp38(117-373aa)-T-R-CKS(171-260)" where T and R are the threonine and arginine residues encoded by the synthetic MluI sites introduced into the vector.

Example 8

Production and Characterization of Recombinant CMV Antigens

Plasmids pCMV-1A, pCMV-3A, pCMV-4, pCMV-9, pCMV-26, pCMV-27, pCMV-28, pCMV-28STOP, and pCMV-29 were transformed separately into competent *E. coli* K-12 strain XL-1 Blue. Bacterial clones expressing the individual HCMV proteins were grown overnight at 37° C. in Superbroth II media containing 100 ug/mL ampicillin. The overnight cultures were diluted 1:100 in the same media and grown at 37° C. with aeration until the culture reached an optical density 0.7-0.9, measured at 600 nm. A pre-induced sample was taken from the culture, centrifuged for 1 minute at 13,000×g, and a crude bacterial lysate was prepared by resuspending the cell pellet in SDS-PAGE loading buffer and boiling for 5 minutes.

The synthesis of recombinant HCMV antigen was induced in each individual culture by the addition of IPTG to a final concentration of 1 mM after the optical density reached 0.7-0.9. A sample was taken from the culture 4 hours post-IPTG induction, the sample was centrifuged for 1 minute at 13,000× g, and a crude bacterial lysate was prepared by re-suspending the cell pellet in SDS-PAGE loading buffer and boiling for 5 minutes. The cells then were harvested at 12,000×g at 4° C. for 15 minutes, and the cell pellets were frozen at −80° C. until further processing.

The pre-induced and post-induced samples were loaded on Daiichi pre-cast 4-20% gradient SDS-PAGE gels. After running, the gels were stained in a solution of 0.125% Coomassie™ blue dye in 50% methanol and 10% acetic acid for 1 hour and then destained in a solution of 7% acetic acid and 5% methanol until a clear background was obtained. Protein molecular weight standards were run on the gel to determine the molecular weight of the recombinant HCMV proteins expressed in *E. coli*.

Step A: Characterization of Recombinant Antigen CKS-A1C2F3-CKS (rpCMV-1A)

Expression of the recombinant protein rpCMV-1A (CKS-A1C2F3-CKS) was evaluated by running pre-induced and post-induced samples obtained from crude lysates of XL-1 Blue cells transformed with pCMV-1A on gradient SDS-PAGE gels. Analysis of the Coomassie™ stained gel indicated that the rpCMV-1A protein comprised 15% of the total cell protein. The recombinant protein had an apparent molecular weight of 44,000, which was larger than the calculated molecular weight of 36,000.

Step B: Characterization of Recombinant Antigen CKS-A1C2F3 (rpCMV-3A)

Expression of the recombinant protein rpCMV-3A (CKS-A1C2F3) was evaluated by running pre-induced and post-induced samples obtained from crude lysates of XL-1 Blue cells transformed with pCMV-3A on gradient SDS-PAGE gels. Analysis of the Coomassie™ stained gel indicated that the rpCMV-3A protein comprised 15% of the total cell protein. The recombinant protein had an apparent molecular weight of 42,000, which was larger than the calculated molecular weight of 34,000.

Step C: Characterization of Recombinant Antigen CKS-A1C2F3-H10 (rpCMV-4)

Expression of the recombinant protein rpCMV-4 (CKS-A1C2F3-H10) was evaluated by running pre-induced and post-induced samples obtained from crude lysates of XL-1 Blue cells transformed with pCMV-4 on gradient SDS-PAGE gels. Analysis of the Coomassie™ stained gel indicated that the rpCMV-4 protein comprised 15% of the total cell protein. The recombinant protein had an apparent molecular weight of 70,000, which was larger than the calculated molecular weight of 58,000.

Step D: Characterization of Recombinant Antigen CKS-pp65 (297-510aa) (rpCMV-9)

Expression of the recombinant protein rpCMV-9 (CKS-pp65(297-510aa)) was evaluated by running pre-induced and post-induced samples obtained from crude lysates of XL-1 Blue cells transformed with pCMV-9 on gradient SDS-PAGE gels. Analysis of the Coomassie™ stained gel indicated that the rpCMV-9 protein comprised 10% of the total cell protein equally distributed between 2 proteins of molecular weight 60,000 and 56,000, both of which were larger than the calculated molecular weight of 51,000.

Step E: Characterization of Recombinant Antigen CKS-pp38 (117-373aa) (rpCMV-26)

Expression of the recombinant protein rpCMV-26 (CKS-pp38(117-373aa)) was evaluated by running pre-induced and post-induced samples obtained from crude lysates of XL-1 Blue cells transformed with pCMV-26 on gradient SDS-PAGE gels. Analysis of the Coomassiem stained gel indicated that the rpCMV-26 protein comprised 10% of the total cell protein. The recombinant protein had an apparent molecular weight of 65,000, which was larger than the calculated molecular weight of 54,000.

Step F: Characterization of Recombinant Antigen CKS-A1C2F3-H10-CKS (rpCMV-27)

Expression of the recombinant protein rpCMV-27 (CKS-A1C2F3-H10-CKS) was evaluated by running pre-induced and post-induced samples obtained from crude lysates of XL-1 Blue cells transformed with pCMV-27 on gradient SDS-PAGE gels. Analysis of the Coomassie™ stained gel indicated that the rpCMV-27 protein comprised 10% of the total cell protein. The recombinant protein had an apparent molecular weight of 72,000, which was larger than the calculated molecular weight of 60,000.

Step G: Characterization of Recombinant Antigen CKS-pp65 (297-510aa)-CKS (rpCMV-28)

Expression of the recombinant protein rpCMV-28 (CKS-pp65(297-510aa)-CKS) was evaluated by running pre-induced and post-induced samples obtained from crude lysates of XL-1 Blue cells transformed with pCMV-28 on gradient SDS-PAGE gels. Analysis of the Coomassie™ stained gel indicated that the rpCMV-28 protein comprised 5% of the total cell protein. The recombinant protein had an apparent molecular weight of 57,000, which was larger than the calculated molecular weight of 53,000.

Step H: Characterization of Recombinant Antigen CKS-pp65 (297-510aa)-STOP-CKS (rpCMV-28STOP)

Expression of the recombinant protein rpCMV-28STOP (CKS-pp65(297-510aa)-STOP-CKS) was evaluated by running pre-induced and post-induced samples obtained from crude lysates of XL-1 Blue cells transformed with pCMV- 28STOP on gradient SDS-PAGE gels. Analysis of the Coomassie™ stained gel indicated that the rpCMV-28STOP protein comprised 5% of the total cell protein. The recombinant protein had an apparent molecular weight of 47,000, which was larger than the calculated molecular weight of 42,000.

Step I: Characterization of Recombinant Antigen CKS-pp38 (117-373aa)-CKS (rpCMV-29)

Expression of the recombinant protein rpCMV-29 (CKS-pp38(117-373aa)-CKS) was evaluated by running pre-induced and post-induced samples obtained from crude lysates of XL-1 Blue cells transformed with pCMV-29 on gradient SDS-PAGE gels. Analysis of the Coomassie™ stained gel indicated that the rpCMV-29 protein comprised 5% of the total cell protein. The recombinant protein had an apparent molecular weight of 67,000, which was larger than the calculated molecular weight of 55,000.

Example 9

Comparison of Embedded and Non-Embedded CKS expression

Crude lysates and purified proteins were prepared from *E. coli* cells for each recombinant antigen expressed in the embedded mode of CKS expression and in the non-embedded mode of CKS expression. This was done in order to directly compare the embedded mode of CKS expression of recombinant antigens with the non-embedded mode of CKS expression. These crude lysates and purified proteins were subsequently analyzed on SDS-PAGE and Western blots as described below. Crude lysates from *E. coli* cells were prepared as described in Example 8.

Purified proteins from *E. coli* cells were prepared by the following general method. The cell pellets described in Example 7 were thawed and homogenized in TEM lysis buffer that contained additional 1 mg/mL lysozyme, 25 mg/nL DNaseI, 2 mg/nL aprotinin. After homogenization, PMSF was added to a final concentration of 0.2 mg/mL and the cells were lysed for 30 minutes at room temperature or 4° C. After lysis the cell lysate was centrifuged at 25,000×g for 30 minutes at 4° C. Soluble *E. coli* proteins and soluble recombinant antigens were found in the supernatant and recombinant antigens that formed insoluble inclusion bodies were found in the pellet. Soluble *E. coli* proteins were removed from the pellet by washing the pellet successively once in PTE buffer that contained additional Triton X-100, once in PTE buffer containing additional 1% sodium deoxycholate, and once in PTE buffer containing additional 0.5 M sodium chloride. The insoluble pellet containing the recombinant antigen was then solubilized in PTE buffer containing additional 8M urea and stored at 4° C.

Crude lysates and purified proteins were analyzed on SDS-PAGE gels as described in Example 8 and on Western blots as described below. After running the SDS-PAGE gels, the proteins were transferred to nitrocellulose membrane using a Semi-Dry Electroblotter™ (Integrated Separation Systems), and the nitrocellulose was blocked overnight using membrane blocking solution. The next day the membrane was incubated with the appropriate mouse monoclonal antibody diluted in Rubazyme specimen dilution buffer for 2 hours at room temperature. After washing the membrane with TBS and TBST, the membrane was then incubated with peroxidase-labelled goat anti-mouse IgG for 1 hour at room temperature. After another washing step with TBS and TBST, the blot was visualized with 4-chloro-1-napththol/hydrogen peroxide.

Step A: Comparison of Expression of CKS-pp65(297-510aa)-CKS (pCMV-28) with CKS-pp65(297-510aa) (pCMV-9)

Evaluation of the crude lysates by SDS-PAGE gels stained with Coomassie™ in Examples 8D and 8G demonstrated that the expression of plasmid pCMV-28 (CKS-pp65(297-510aa)-CKS) produced a single predominant protein band of molecular weight 57,000 dalton upon induction with IPTG, whereas expression of plasmid pCMV-9 (CKS-pp65(297-510aa)) produced a doublet band at 60,000 and 56,000 daltons. In order to further understand the protein products produced after induction with these constructs, Western blot analysis was performed on these crude lysates, and on crude lysate obtained from plasmid pCMV-28STOP (CKS-pp65 (297-510aa)-STOP-CKS) (see Example 8H). The presence of the stop codon in this constuct results in the formation of a truncation protein which does not contain the last 90 amino acids of CKS.

Lysates from these three constructs were probed with a monoclonal antibody directed against CKS and with a monoclonal antibody directed against pp65. The results of Western blot analysis of the recombinant proteins rpCMV-28STOP, rpCMV-28, and rpCMV-9 are shown below in Table 1. Expression of plasmids pCMV-28STOP, pCMV-28, and pCMV-9 in *E. coli* resulted in the formation of the expected full-length proteins. Additionally, a range of protein truncation products, immunoreactive to both the CKS and pp65 monoclonal antibodies, were observed. The size and number of truncation products varied for each protein.

TABLE 1

Molecular Weights as Determined by Western Blotting

| | | Molecular Weight of Major Immunoreactive Bands (kD) | |
|---|---|---|---|
| Construct | Type | CKS Mab | pp65 Mab |
| pCMV-28STOP (CKS-pp65-STOP-CKS) | Truncated | None | 47-41 |
| pCMV-28 (CKS-pp65-CKS) | Embedded | 57 | 57, 47-41 |
| pCMV-9 (CKS-pp65) | Non-Embedded | 59, 55, 54-33 | 59, 55, 48 |

Expression of plasmid pCMV-28STOP in *E. coli* resulted in the production of the expected full-length protein (rpCMV-28STOP at 47 kD) plus a range of truncation products detectable with the pp65 monoclonal antibody. No protein products were detected with the CKS monoclonal antibody. This result demonstrated that the epitope recognized by the CKS monoclonal antibody was located in the C-terminal portion of the CKS protein, as amino acids 171-260 are not present in this protein due to the presence of the stop codon downstream of the pp65 gene.

Embedded expression of plasmid pCMV-28 in *E. coli* resulted in the production of the expected full-length protein (57 kD) detected by both the CKS monoclonal antibody and the pp65 monoclonal antibody. The truncation products of plasmid pCMV-28 (from 47 to 41 kD), however, were only detected by the pp65 monoclonal antibody. This was due to the fact that these truncation products had lost the epitope reactive with the CKS monoclonal antibody.

It was observed that a 10 kD gap existed between the full-length protein (at 57 kD) from plasmid pCMV-28 and the truncation products of plasmid pCMV-28 (from 47 to 41 kD), all of which were immunoreactive with the pp65 monoclonal antibody. It was also important to note that the truncation products produced by plasmids pCMV-28STOP and pCMV-28 which were immunoreactive with the pp65 monoclonal antibody were identical in size. Hence, during embedded CKS expression in *E. coli,* either (i) the full-length protein product was made or (ii) truncation products were made which were 10 kD or more smaller which lacked the C-terminus of CKS (amino acids 171-260), presumably due to ribosome pausing during translation of the embedded gene.

While not wishing to be limited by theory, it was believed that during translation of the embedded fusion gene in *E. coli* one of two things had taken place. Either the ribosome had "stalled" during translation of the embedded gene inside the CKS gene, resulting in the production of protein truncation products, or the ribosome had successfully translated the embedded gene and continued through the rest of the CKS gene. This was in contrast to the non-embedded expression of plasmid pCMV-9 in *E. coli,* where no 10 kD gap existed between the full-length protein (59 kD) and the largest truncation product (55 kD) as detected by both monoclonal antibodies.

These results demonstrate two advantages of embedded CKS expression over non-embedded CKS expression. First, embedded CKS expression shifted the size of the contaminating truncation products by 10 kD, thus improving the chromatographic separation of full-length protein from truncated products when using standard chromatographic techniques. Second, use of the CKS monoclonal antibody directed to the C-terminus of CKS, and the size of the purified protein, could be used to prove from Western blot data of the purified proteins produced by embedded CKS expression that the embedded epitopes were intact. The CKS amino acid sequence (amino acids 171-260) on the end of this embedded CKS expressed protein served as an immunological "tag" that could be visualized on a Western blot with the CKS monoclonal antibody. Its presence ensured that the embedded epitopes were intact in the purified protein. Any raggedness of the C-terminal end of such a protein would be confined to the immunologically irrelevant CKS portion.

Step B: Comparison of Expression of CKS-A1C2F3-H10-CKS (pCMV-27) with CKS-A1C2F3-H10 (pCMV-4)

Evaluation of the crude lysates by SDS-PAGE gels stained with Coomassie™ in Examples 8C and 8F demonstrated that the expression of plasmids pCMV-27 (CKS-A1C2F3-H10-CKS) and pCMV-4 (CKS-A1C2F3-H10) produced a single predominant protein band of molecular weight of 70,000-72,000 daltons upon induction with IPTG.

Western blot analysis was performed on crude lysates obtained from the expression of these constructs in *E. coli* in order to further characterize the protein products. Lysates from these two constructs were probed with a monoclonal antibody directed against CKS and with a monoclonal antibody directed against H10. The results of this analysis are shown below in Table 2.

TABLE 2

Molecular Weights as Determined by Western Blotting

| Construct | Type | Molecular Weight of Major Immunoreactive Bands (kD) | |
| --- | --- | --- | --- |
| | | CKS Mab | H10 Mab |
| pCMV-27 (CKS-A1C2F3-H10-CKS) | Embedded | 68 | 68, 58-48 |
| pCMV-4 (CKS-A1C2F3-H10) | Non-Embedded | 68, 66-40 | 68, 66-56 |

As seen in Table 2, expression of plasmids pCMV-27 and pCMV-4 proteins in *E. coli* resulted in the formation of the expected full-length protein, plus a range of protein truncation products, which were immunoreactive to both the CKS and H10 monoclonal antibodies.

Embedded CKS expression of A1C2F3-H10 in *E. coli* resulted in the production of the full-length protein (68 kD) and a range of truncation products (from 58 to 48 kD) immunoreactive with the H10 monoclonal antibody. The contaminating truncation products produced from embedded CKS expression were separated by 10 kD in size from the full-length protein. In contrast, non-embedded CKS expression of A1C2F3-H10 in *E. coli* resulted in the production of the full-length protein (68 kD) and a range of protein truncation products (from 66 to 56 kD) immunoreactive with the H10 monoclonal antibody. The contaminating protein truncation products produced from non-embedded CKS expression were not well separated in size from the full-length protein.

The full-length proteins produced from embedded and non-embedded CKS expression and the protein truncation products produced from non-embedded CKS expression were immunoreactive with the CKS monoclonal antibody. The contaminating protein products produced from embedded CKS expression were not immunoreactive with the CKS monoclonal antibody as the CKS monoclonal antibody was specific for the C-terminus of CKS.

Embedded CKS expression shifted the size of the contaminating truncation products by 10 kD, thus improving the chromatographic separation of full-length protein from truncated product when using standard chromatographic techniques. The CKS amino acid sequence (amino acids 171-260) on the end of this embedded CKS expressed protein again served as an immunological tag, visualizable on a Western blot with the anti-CKS monoclonal antibody, showing that the embedded epitopes were intact in the purified protein.

Step C: Comparison of Expression of CKS-A1C2F3-CKS (pCMV-1A) with CKS-A1C2F3 (pCMV-3A)

Evaluation of the crude lysates by SDS-PAGE gels stained with Coomassie™ in Examples 8A and 8B demonstrated that the expression of plasmids pCMV-1A (CKS-A1C2F3-CKS) and pCMV-3A (CKS-A1C2F3) produced a single predominant protein band of molecular weight of 42,000-44,000 daltons upon induction with IPTG. Analysis of the Coomassie™ stained gel indicated that the rpCMV-1A and rpCMV-3A proteins each comprised 15% of the total cell protein.

The rpCMV-3A protein, obtained by non-embedded CKS expression of plasmid pCMV-3A was located entirely within the supernatant obtained after centrifugation of the cell lysate. This protein was approximately 15% pure as determined by SDS-PAGE. In contrast, the rpCMV-1A protein, obtained by embedded CKS expression of plasmid pCMV-1A, was located entirely within the pellet obtained after centrifugation of the cell lysate. The inclusion bodies obtained by expression of plasmid pCMV-1A were purified by washing as described above. The inclusion bodies were solubilized in 8M urea and rpCMV-1A was determined to be 85-90% pure by SDS-PAGE. The embedded CKS expression of rpCMV-1A was the preferred mode of CKS expression over non-embedded CKS expression. The purification of rpCMV-1A was greatly simplified due to the altered solubility of the protein produced by the embedded CKS expression.

Hence, non-embedded CKS expression of the A1C2F3 epitope cluster (in plasmid pCMV-3A) resulted in the production of a soluble recombinant antigen, while embedded CKS expression of A1C2F3 (in plasmid pCMV-1A) resulted in the production of an insoluble recombinant antigen. These results demonstrate another potential advantage of the embedded CKS expression method of the present invention over non-embedded CKS expression, in that the purification of recombinant proteins may be greatly simplified due to the altered solubility of the proteins when produced by embedded CKS expression.

Step D: Comparison of Expression of CKS-pp38(117-373aa)-CKS (pCMV-29) with CKS-pp38(117-373aa) (pCMV-26)

Evaluation of the crude lysates by SDS-PAGE gels stained with Coomassie™ in Examples 7E and 7I demonstrated that the expression of plasmids pCMV-29 (CKS-pp38(117-373aa)-CKS) and pCMV-26 (CKS-pp38(117-373aa)) produced a single predominant protein band of molecular weight of 65,000-67,000 daltons upon induction with IPTG. Analysis of the Coomassie™ stained gel indicated that the rpCMV-29 and rpCMV-26 proteins comprised 5% and 10% of the total cell protein, respectively.

The rpCMV-26 protein, obtained by non-embedded CKS expression of plasmid pCMV-26, was located entirely within the supernatant obtained after centrifugation of the cell lysate. This protein was approximately 10% pure as determined by SDS-PAGE. In contrast, the rpCMV-29 protein, obtained by embedded CKS expression of plasmid pCMV-29, was located entirely within the pellet obtained after centrifugation of the cell lysate. The inclusion bodies obtained by expression of plasmid pCMV-29 were purified by washing as described above. The inclusion bodies were solubilized in 8M urea, and rpCMV-29 was determined to be 85-90% pure by SDS-PAGE. Hence, non-embedded CKS expression of amino acids 117-373 of pp38 (in plasmid pCMV-26) resulted in the production of a soluble recombinant antigen, while embedded CKS expression of that protein sequence (in plasmid pCMV-29) resulted in the production of an insoluble recombinant antigen.

These results again that the purification of recombinant proteins may be greatly simplified due to the altered solubility of the proteins when produced by embedded CKS expression.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. For example, it is expected that any number of sites within the CKS carrier protein would permit embedded expression of heterologous proteins. Moreover, it is believed that multiple sites at different positions in a CKS or other carrier protein could be used for the simultaneous embedded expression of various heterologous proteins. Such "segmented expression", in which epitopes are embedded at different sites in the carrier protein, might permit improved levels of expression. Segmented expression of heterologous proteins could also be expected to minimize steric hindrance between immunoglobulins attempting to bind at approximately the same region of the fusion protein. In yet another variation of the invention, a polylinker sequence might be inserted into the carrier protein gene to facilitate the insertion of various heterologous protein-encoding DNA. Furthermore, while the construction of plasmids in the above examples demonstrates a certain type of ligation (blunt/sticky), other types (blunt/blunt, or sticky/sticky) might also be used. Such changes and modifications, including without limitation those relating to the expression methods, confirmatory methods, fusion proteins, DNA constructs, plasmid vectors and transformed host cells of the invention and the uses thereof, may be made without departing from the spirit and scope thereof.

What is claimed is:

1. A method for expressing an insoluble fusion protein of a heterologous protein and a carrier protein in an inclusion body of a prokaryotic host cell, comprising the steps of:
   (a) providing a DNA vector having:
      (1) a control region operatively linked to a first genetic element encoding a carrier protein constituting a first and a second domain, said first domain comprising the N-terminal portion of said carrier protein and said second domain comprising the C-terminal portion of said carrier protein, capable of expression in the host cell, and
      (2) a second genetic element encoding the heterologous protein, the second element being embedded within the first element such that the first and the second elements are contiguous and in the same reading frame;
   (b) transforming the host cell with the DNA vector; and,
   (c) expressing an insoluble fusion protein of the heterologous protein and the carrier protein, wherein the heterologous protein is joined at its N-terminus to the first domain of the carrier protein and at its C-terminus to the second domain of the carrier protein, where the first domain is sufficiently long to permit expression of the heterologous protein and the second domain is sufficiently long to permit separation, based on apparent molecular weight, of the fusion protein from expression products comprising some or all the heterologous protein but lacking the second domain, and wherein said fusion protein is located in an inclusion body of said host cell.

2. A method according to claim 1 wherein the heterologous protein is a bacterial protein.

3. A method according to claim 1 wherein the heterologous protein is a viral protein.

4. A method according to claim 1 wherein the control region comprises a prokaryotic promoter and a prokaryotic ribosomal binding site.

5. A method according to claim 4 wherein the control region comprises a lac operon.

6. A method according to claim 1 wherein the carrier protein is a CKS protein.

7. A method according to claim 6 wherein the heterologous protein is an a human cytomegalovirus (HCMV) protein.

8. A method according to claim 7 wherein the heterologous protein comprises an immunologically reactive portion of a viral protein selected from the group consisting of HCMV proteins pp38, pp52, pp65 and pp150.

9. A method according to claim 7 wherein the heterologous protein comprises an immunogenic portion of HCMV protein pp38.

10. A method according to claim 7 wherein the heterologous protein comprises an immunogenic portion of HCMV protein p65.

11. A method according to claim 7 wherein the heterologous protein comprises an immunogenic portion of an epitope selected from the group consisting of HCMV epitopes H10, F3 and A1C2.

12. A DNA construct for insertion into a plasmid vector, comprising
  (a) a control region operatively linked to a first genetic element encoding a carrier protein capable of expression in a host cell, and
  (b) a second genetic element encoding a heterologous protein, the second element being embedded within the first element such that the first and second elements are contiguous and in the same reading frame, wherein the DNA construct, upon transformation of a prokaryotic host cell with the plasmid vector, directs the expression of an insoluble fusion protein of the heterologous protein and the carrier protein wherein the heterologous protein is joined at its N-terminus to a first domain of the carrier protein and at its C-terminus to a second domain of the carrier protein the second domain being of sufficient length to permit separation, based on apparent molecular weight, of the fusion protein from the expression products comprising some or all the heterologous protein but lacking the second domain, wherein said insoluble fusion protein is located in an inclusion body of said host cell.

13. A DNA construct according to claim 12 wherein the heterologous protein is a bacterial protein.

14. A DNA construct according to claim 12 wherein the heterologous protein is a viral protein.

15. A DNA construct according to claim 12 wherein the control region comprises a prokaryotic promoter and a prokaryotic ribosomal binding site.

16. A DNA construct according to claim 15 wherein the control region comprises a lac operon.

17. A DNA construct according to claim 12 wherein the carrier protein is a CKS protein.

18. A DNA construct according to claim 17 wherein the heterologous protein is a human cytomegalovirus (HCMV) protein.

19. A DNA construct according to claim 18 wherein the heterologous protein comprises an immunologically reactive portion of a viral protein selected from the group consisting of HCMV proteins pp38, pp52, pp65 and pp150.

20. A DNA construct according to claim 18 wherein the heterologous protein comprises an immunogenic portion of HCMV protein pp38.

21. A DNA construct according to claim 18 wherein the heterologous protein comprises an immunogenic portion of HCMV protein p65.

22. A DNA construct according to claim 18 wherein the heterologous protein comprises an immunogenic portion of an epitope selected from the group consisting of HCMV epitopes H10, F3 and A1C2.

\* \* \* \* \*

UNITED STATES PATENT AND TRADEMARK OFFICE
CERTIFICATE OF CORRECTION

| | | |
|---|---|---|
| PATENT NO. | : 7,901,910 B2 | Page 1 of 1 |
| APPLICATION NO. | : 08/742619 | |
| DATED | : March 8, 2011 | |
| INVENTOR(S) | : Maine et al. | |

It is certified that error appears in the above-identified patent and that said Letters Patent is hereby corrected as shown below:

Title Page, Item (54) and at Column 1, lines 1 and 2, title: "Embedded Expression of Insoluble Heterologous Proteins" to read as --Embedded Expression of Heterologous Proteins--

Column 31, line 04, claim 7: "an a human" to read as --a human--

Column 31, line 14, claim 10: "p65." to read as --pp65.--

Column 31, line 20, claim 12: "comprising" to read as --comprising:--

Column 31, line 34, claim 12: "protein the second domain being" to read as --protein, the second domain being--

Column 32, line 29, claim 21: "p65." to read as --pp65.--

Signed and Sealed this
Thirty-first Day of July, 2012

David J. Kappos
*Director of the United States Patent and Trademark Office*

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: genomic DNA (xi) SEQUENCE DESCRIPTION: SEQ ID NO: 1:

```
GGATAACAAT TGGGCATCCA GTAAGGAGGT                                        30
```

(2) INFORMATION FOR SEQ ID NO: 2:

(i) SEQUENCE CHARACTERISTICS:
      (A) LENGTH: 106 base pairs
      (B) TYPE: nucleic acid
      (C) STRANDEDNESS: single
      (D) TOPOLOGY: linear (ii) MOLECULE TYPE: genomic DNA (xi) SEQUENCE DESCRIPTION: SEQ ID NO: 2:

```
AGGATGCGGA TCCCCGATCT CGACCCGTCG ACGAATTCGA GCTCGGTACC CGGGGATCCT       60

CTAGACTGCA GGCATGCTAA GTAAGTAGAT CGGGAATTCA CATCCG                    106
```

(2) INFORMATION FOR SEQ ID NO: 3:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 3:

```
Lys Leu Gln Glu Phe
1               5
```

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 4:

```
CCC GCG CGC TAC GCG TCG ACG CGT CTG CCC                          30
Pro Ala Arg Tyr Ala Ser Thr Arg Leu Pro
1               5                   10
```

(2) INFORMATION FOR SEQ ID NO: 5:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 5:

```
GAATTAATTC CCATTAATGT GAGTTAGCTC ACTCATTAGG CACCCCAGGC TTTACACTTT      60

ATGTTCCGGC TCGTATTTTG TGTGGAATTG TGAGCGGATA ACAATTGGGC ATCCAGTAAG     120

GAGGTTTAA ATG AGT TTT GTG GTC ATT ATT CCC GCG CGC TAC GCG TCG ACG    171
          Met Ser Phe Val Val Ile Ile Pro Ala Arg Tyr Ala Ser Thr
          1               5                   10

CGT CTG CCC GGT AAA CCA TTG GTT GAT ATT AAC GGC AAA CCC ATG ATT      219
Arg Leu Pro Gly Lys Pro Leu Val Asp Ile Asn Gly Lys Pro Met Ile
15              20                  25                  30

GTT CAT GTT CTT GAA CGC GCG CGT GAA TCA GGT GCC GAG CGC ATC ATC      267
Val His Val Leu Glu Arg Ala Arg Glu Ser Gly Ala Glu Arg Ile Ile
                35                  40                  45

GTG GCA ACC GAT CAT GAG GAT GTT GCC CGC GCC GTT GAA GCC GCT GGC      315
Val Ala Thr Asp His Glu Asp Val Ala Arg Ala Val Glu Ala Ala Gly
            50                  55                  60

GGT GAA GTA TGT ATG ACG CGC GCC GAT CAT CAG TCA GGA ACA GAA CGT      363
Gly Glu Val Cys Met Thr Arg Ala Asp His Gln Ser Gly Thr Glu Arg
        65                  70                  75

CTG GCG GAA GTT GTC GAA AAA TGC GCA TTC AGC GAC GAC ACG GTG ATC      411
Leu Ala Glu Val Val Glu Lys Cys Ala Phe Ser Asp Asp Thr Val Ile
    80                  85                  90

GTT AAT GTG CAG GGT GAT GAA CCG ATG ATC CCT GCG ACA ATC ATT CGT      459
Val Asn Val Gln Gly Asp Glu Pro Met Ile Pro Ala Thr Ile Ile Arg
95                  100                 105                 110

CAG GTT GCT GAT AAC CTC GCT CAG CGT CAG GTG GGT ATG ACG ACT CTG      507
Gln Val Ala Asp Asn Leu Ala Gln Arg Gln Val Gly Met Thr Thr Leu
```

-continued

```
              115                 120                 125
GCG GTG CCA ATC CAC AAT GCG GAA GAA GCG TTT AAC CCG AAT GCG GTG        555
Ala Val Pro Ile His Asn Ala Glu Glu Ala Phe Asn Pro Asn Ala Val
            130                 135                 140

AAA GTG GTT CTC GAC GCT GAA GGG TAT GCA CTG TAC TTC TCT CGC GCC        603
Lys Val Val Leu Asp Ala Glu Gly Tyr Ala Leu Tyr Phe Ser Arg Ala
        145                 150                 155

ACC ATT CCT TGG GAT CGT GAT CGT TTT GCA GAA GGC CTT GAA ACC GTT        651
Thr Ile Pro Trp Asp Arg Asp Arg Phe Ala Glu Gly Leu Glu Thr Val
        160                 165                 170

GGC GAT AAC TTC CTG CGT CAT CTT GGT ATT TAT GGC TAC CGT GCA GGC        699
Gly Asp Asn Phe Leu Arg His Leu Gly Ile Tyr Gly Tyr Arg Ala Gly
175                 180                 185                 190

TTT ATC CGT CGT TAC GTC AAC TGG CAG CCA AGT CCG TTA GAA CAC ATC        747
Phe Ile Arg Arg Tyr Val Asn Trp Gln Pro Ser Pro Leu Glu His Ile
            195                 200                 205

GAA ATG TTA GAG CAG CTT CGT GTT CTG TGG TAC GGC GAA AAA ATC CAT        795
Glu Met Leu Glu Gln Leu Arg Val Leu Trp Tyr Gly Glu Lys Ile His
            210                 215                 220

GTT GCT GTT GCT CAG GAA GTT CCT GGC ACA GGT GTG GAT ACC CCT GAA        843
Val Ala Val Ala Gln Glu Val Pro Gly Thr Gly Val Asp Thr Pro Glu
        225                 230                 235

GAT CTC GAC CCG TCG ACG AAT TCG AGC TCG GTA CCC GGG GAT CCT CTA        891
Asp Leu Asp Pro Ser Thr Asn Ser Ser Ser Val Pro Gly Asp Pro Leu
    240                 245                 250

GAC TGC AGG CAT GCT AAG TAAGTAGATCT                                    920
Asp Cys Arg His Ala Lys
255                 260

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 6:

CCC GCG CGC TAC GCG ACG TCG CGT CTG CCC                                30
Pro Ala Arg Tyr Ala Thr Ser Arg Leu Pro
1               5                   10
```